(12) United States Patent
Yan et al.

(10) Patent No.: US 7,030,292 B2
(45) Date of Patent: Apr. 18, 2006

(54) METHOD FOR PRODUCING A POPULATION OF HOMOZYGOUS STEM CELLS HAVING A PRE-SELECTED IMMUNOTYPE AND/OR GENOTYPE, CELLS SUITABLE FOR TRANSPLANT DERIVED THEREFROM, AND MATERIALS AND METHODS USING SAME

(75) Inventors: Wen Liang Yan, Potomac, MD (US); Steve Chien-Wen Huang, Germantown, MD (US); Minh-Thanh Nguyen, Rockville, MD (US); Huan (Helen) Lin, N. Potomac, MD (US); Jingqi Lei, Gaithersburg, MD (US); Ruchi Khanna, Germantown, MD (US)

(73) Assignee: Stemron, Inc., Myersville, MD (US)

(*) Notice: Subject to any disclaimer, the term of this patent is extended or adjusted under 35 U.S.C. 154(b) by 0 days.

(21) Appl. No.: 10/032,495

(22) Filed: Jan. 2, 2002

(65) Prior Publication Data

US 2002/0155601 A1 Oct. 24, 2002

Related U.S. Application Data

(60) Provisional application No. 60/258,881, filed on Jan. 2, 2001.

(51) Int. Cl.
 *C12N 15/00* (2006.01)
 *C12N 5/00* (2006.01)
 *C12N 5/02* (2006.01)
 *A01N 65/00* (2006.01)

(52) U.S. Cl. .................. 800/24; 424/93.1; 435/325; 435/373; 435/376; 435/377

(58) Field of Classification Search .............. 424/93.1; 435/325, 373, 376, 377; 800/22
 See application file for complete search history.

(56) References Cited

U.S. PATENT DOCUMENTS

| | | | |
|---|---|---|---|
| 5,503,980 A | 4/1996 | Cantor | |
| 5,683,880 A | 11/1997 | Kamb | |
| 5,683,881 A | 11/1997 | Skiena | |
| 5,750,345 A | 5/1998 | Bowie | |
| 5,843,780 A | 12/1998 | Thomson | |
| 5,905,042 A | 5/1999 | Stice et al. | |
| 5,945,577 A | 8/1999 | Stice et al. | |
| 6,025,136 A | 2/2000 | Drmanac | |
| 6,077,710 A | 6/2000 | Susko-Parrish et al. | |
| 6,100,030 A | 8/2000 | Feazel et al. | |
| 6,141,657 A | 10/2000 | Rothberg et al. | |
| 6,235,970 B1 * | 5/2001 | Stice et al. ............ | 800/24 |
| 2004/0091936 A1 | 5/2004 | West | |

FOREIGN PATENT DOCUMENTS

| | | |
|---|---|---|
| WO | WO 90/03432 | 4/1990 |
| WO | WO 94/24274 | 10/1994 |
| WO | WO 94/26884 | 11/1994 |
| WO | WO 94/26889 | 11/1994 |
| WO | WO 98/07841 | 2/1998 |
| WO | WO 00/12682 | 3/2000 |
| WO | WO 01/29206 | 4/2001 |
| WO | WO 01/30978 | 5/2001 |
| WO | WO 01/79445 | 10/2001 |
| WO | WO 01/84920 | 11/2001 |
| WO | WO 02/102997 A2 | 12/2003 |

OTHER PUBLICATIONS

Donovan and Gearhart, Nat 2001 Nov.;414:92-97.*
Newman-Smith et al, Development 1995;121:2069-77.*
Park et al, Jpn J Vet Res 1998;46:19-28.*
Draper et al, Curr Opin Obstet Gynecol 2002;14:309-315.*
Odorico et al, Stem Cells 2001;19:193-204.*
Alberts et al, Molecular Biol Cell 1994.*
Liu et al, Acta Zoologica Sinica 1998;44;247-8.*
Mitalipov et al, Biol Reprod 2001;65:253-9.*
Gearhart, Science 1998;282: 1061-2.*
Ohnuma et al, J Hematother Stem Cell Res 2000;9:541-550.*
Kaufman, M.H., et al., "Establishment of pluripotential cell lines from haploid mouse embryos," *J. Embryol. Exp. Morphol.*, 73:249-61 (1983).
Lin, H. et al., "Multilineage Potential of Homozygous Stem Cells Derived from Metaphase II Oocytes", *Stem Cells*, 21:152-161 (2003).
International Search Report, Jun. 18, 2003, PCT/US 02/00107.
Allen, N. D., et al., "A functional analysis of imprinting in parthenogenetic embryonic stem cells", *Development*, 120: 1473-82 (1994).

(Continued)

*Primary Examiner*—Q. Janice Li
(74) *Attorney, Agent, or Firm*—Reed Smith, LLP

(57) ABSTRACT

A method of producing a homogenous population of homozygous stem (HS) cells pre-selected for immunotype and/or genotype from donor cells is described herein. The invention relates to methods of using immunohistocompatible HS cells for diagnosis, therapeutic and cosmetic transplantation, and the treatment of various genetic diseases, neurodegenerative diseases, traumatic injuries and cancer. The invention further relates to methods for using histocompatible HS stem cells pre-selected for a non-disease genotype for prophylactic and therapeutic intervention including, but not limited to, therapeutic and cosmetic transplantation, and the treatment of various genetic diseases, neurodegenerative diseases, and cancer. Furthermore, the invention relates to a catalogued transplant depository of HS cells derived from multiple donors, each of the HS cells being homozygous for a unique HLA haplotype, for the purpose of having a constant, reliable, comprehensive supply of immunohistocompatible cells for diagnosis, treatment and/or transplantation.

3 Claims, 13 Drawing Sheets

OTHER PUBLICATIONS

Figure 1:
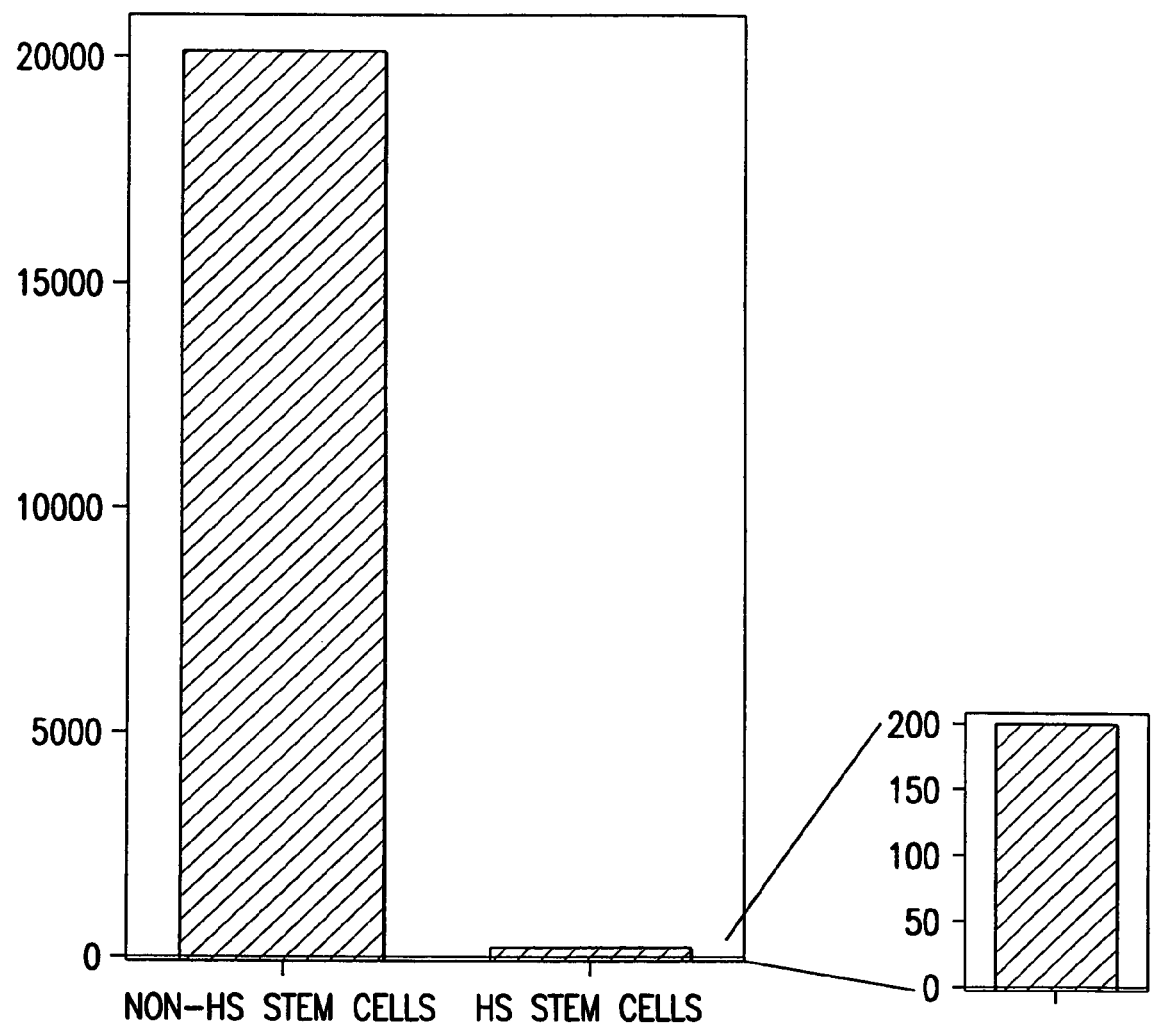

Andrews, P. W., "Teratocarcinomas and human embryology: Pluripotent human EC cell lines", *APMIS* 106: 158-68 (1998).

Asakura, S. and Abe, S., "Synacrosomal Formation after Cell Fusion of Round Spermatids of Xenopus laevis", *Experimental Cell Research* 181:566-73 (1989).

Assady, S., et al. "Insulin Production by Human Embryonic Stem Cells", *Diabetes* 50: 1691-97 (2001).

Bach et al. (1964), *Lymphocyte Interaction: A Potential Histocompatibility Test In Vitro*, Science 143:813-814.

Bains, W., et al., "A Novel Method For Nucleic Acid Sequence Determination", J. Theoret. Biol., 135: 303-307 1988.

Barriere, P. and Lopes, P., "Fecondation in vitro: stimulation de l'ovulation et recueil des ovocytes", *Rev Prat* 40(29): 2689-93 (1990).

Borlongan, C.V., et al. "Cerebral ischemia and CNS transplantation: differential effects of grafted fetal rat striatal cells and human neurons derived from a clonal cell line", *NeuroReport* 9(16): 3703-09 (1998).

Botstein et al., "Construction of a Genetic Linkage Map in Man Using Restriction Fragment Length Polymorphisms", Am. J. Hum. Genet. 32:314-331, 1980.

Bottero, L., et al., "Differential Activation of Homeobox Genes by Retinoic Acid in Human Embryonal Carcinoma Cells", *Recent Results in Cancer Research* 123: 133-43 (1991).

Bradley, A., et al., "Formation of germ-line chimaeras from embryo-derived teratocarcinoma cell lines", *Nature* 309: 255-56 (1984).

Brustle, O., et al., "Embryonic Stem Cell-Derived Glial Precursors: A Source of Myelinating Transplants", *Science* 285: 754-56 (1999).

Campbell, K. H. S., et al., "Sheep cloned by nuclear transfer from a cultured cell line", *Nature* 380: 64-66 (1996).

Carritt, B., et al., "Diverse origins of multiple ovarian teratomas in a single individual", *P. N. A. S.* USA 79:7400-04 (1982).

Cherny, R.A., et al., "Strategies for the Isolation and Characterization of Bovine Embryonic Stem Cells", *Reprod. Fertil. Dev.* 6:569-75 (1994).

Cho, S. K., et al., "Functional characterization of B lymphocytes generated in vitro from embryonic stem cells", *P. N. A. S. USA* 96:9797-9802 (1999).

Chomczynski, P. and Sacchi, N., "Single-Step Method of RNA Isolation by Acid Guanidinium Thiocyanate-Phenol-Chloroform Extraction", *Anal Biochem* 162: 156-59 (1987).

Collas, P. and Barnes, F. L., "Nuclear Transplantation by Microinjection of Inner Cell Mass and Granulosa Cell Nuclei", *Molecular Reproduction and Development* 38: 264-67 (1994).

Conner et al., "Detection of Sickle Cell $\beta^S$-globin allele by Hybridization with Synthetic Oligonucleotides", Proc. Natl. Acad. Sci. USA 80:278-282, 1983.

Dahl, N., et al., "Benign Ovarian Teratomas, An Analysis of Their Cellular Origin", *Cancer Genet Cytogenet* 46: 115-23 (1990).

Dani, C., "Embryonic Stem Cell-Derived Adipogenesis", *Cells Tissues Organs* 165: 173-80 (1999).

Dani, C., et al., "Differentiation of embryonic stem cells into adipocytes in vitro", *J Cell Sci* 110(Pt. 11): 1279-85 (1997).

Deka, R., et al., "Genetics and Biology of Human Ovarian Tetratomas. II. Molecular Analysis of Origin of Nondisjunction and Gene-Centromere Mapping of Chromosome I Markers", *Am. J. Hum. Genet.* 47:644-55 (1990).

Doetschman, T., et al., "Establishment of Hamster Blastocyst-Derived Embryonic Stem (ES)Cells", *Developmental Biology* 127:224-27 (1988).

Doetschman, T.C., et al., "The in vitro development of blastocyst-derived embryonic stem cell lines: formation of visceral yolk sac, blood islands and myocardium", *J. Embryol Exp Morphol* 87: 27-45 (1985).

Edwards, B. E., et al., "The Human pluripotent stem cell: impact on medicine and society", *Fertility and Sterility* 74(1) 1-14 (2000).

Eppig, J. T. and Eicher, E. M., "Application of the Ovarian Teratoma Mapping Method in the Mouse", *Genetics* 103: 797-812 (1983).

Eppig, J.T. and Eicher, E. M., "Analysis of Recombination in the Centromere Region of Mouse Chromosome 7 Using Ovarian Teratoma and Backcross Methods", *Journal of Heredity* 79: 425-29 (1988).

Evans, M. J. and Kaufman, M. H., "Establishment in culture of pluripotential cells from mouse embryos", *Nature* 292: 154-56 (1981).

Fairchild, P.J., et al., "Directed differentiation of dendritic cells from mouse embryonic stem cells" *Current Biology* 10(23): 1515-18 (2000).

Fischer et al., "DNA fragments differing by single base-pair substitutions are separated in denaturing gradient gels: Cooerespondence with melting theory," Proc. Natl. Acad. Sci. USA 80:1579-1583, 1983.

Gardner, D. K., and Schoolcraft, W. B., "Culture and Transfer of Human Blastocysts", *Current Opinions in Obstetrics and Gynecology* 11:307-11 (1999).

Gibbs et al., "Detection of single DNA base differences by competitive oligonucleotide priming", Nucleic Acids Res. 17:2437-2448, (1989).

Guan, K., et al., "Embryonic stem cell-derived neurogenesis: Retinoic acid induction and lineage selection of neuronal cells", *Cell Tissue Res* 305:171-76 (2001).

Gulyas, B.J., et al., "Fusion of Oocytes and Development of Oocyte Fusion Products in the Mouse", *Developmental Biology* 101(1):246-50 (1984).

Gulyas, B.J., "Oocyte Fusion," Dev Biol. 4:57-80 (1986).

Gussoni, E., et al., "Dystrophin expression in the mdx mouse restored by stem cell transplantation", *Nature* 401: 390-94 (1999).

Hamazaki, T., et al., "Hepatic maturation in differentiating embryonic stem cells in vitro", *FEBS Letters* 497:15-19 (2001).

Hancock, C.R., et al., "Neuronal Differentiation of Cryopreserved Neural Progenitor Cells Derived from Mouse Embryonic Stem Cells", *Biochemical and Biophysical Research Communications* 271:418-21 (2000).

Handyside, A., et al., "Towards the isolation of embryonal stem cell lines from the sheep", *Roux's Arch. Dev. Biol.* 196:185-90 (1987).

Hansen, J.A., et al., "*Marrow transplants from unrelated donors*," Transplant Proc., Jun.; 26:1710-1712 (1994).

Hogan et al, "Manipulating the mouse embryo: A Laboratory Manual," second edition, Cold Spring Harbor Laboratory Press, pp. 43-45 (1994).

Hogan et al, "Manipulating the mouse embryo: A Laboratory Manual," second edition, Cold Spring Harbor Laboratory Press, pp. 130-132 (1994).

Hogan et al, "Manipulating the mouse embryo: A Laboratory Manual," second edition, Cold Spring Harbor Laboratory Press, pp. 148-150 (1994).
Hogan, et al, "Manipulating the mouse embryo: A Laboratory Manual," second edition, Cold Spring Harbor Laboratory Press, pp. 183-184 (1994).
Hogan, et al, "Manipulating the mouse embryo: A Laboratory Manual," second edition, Cold Spring Harbor Laboratory Press, pp. 254-262 (1994).
Hogan, et al, "Manipulating the mouse embryo: A Laboratory Manual," second edition, Cold Spring Harbor Laboratory Press, pp. 265-272 (1994).
Hogan, et al, "Manipulating the mouse embryo: A Laboratory Manual," second edition, Cold Spring Harbor Laboratory Press, pp. 279-281 (1994).
Hogan, et al, "Manipulating the mouse embryo: A Laboratory Manual," second edition, Cold Spring Harbor Laboratory Press, pp. 283 (1994).
Hole, N., "Embryonic Stem Cell-Derived Hematopoiesis", *Cells Tissues Organs* 165: 181-89 (1999).
Hole, N. and Graham, G. J., "Use of embryonal stem cells in studies of molecular haemopoiesis", *Ballier's Hematology* 10(3):467-83 (1997).
Hole, N. et al., "A Limited Temporal Window for the Derivation of Multilineage Repopulating Hematopoietic Progenitors During Embryonal Stem Cell Differentiation In Vitro", *Blood* 88(4):1266-76 (1996).
Hui et al, *Handbook of HLA Typing Techniques*, p. 9-11 (1993).
Hui et al, *Handbook of HLA Typing Techniques*, p. 99-109 (1993).
Hui et al, *Handbook of HLA Typing Techniques*, p. 118-123 (1993).
Hui et al, *Handbook of HLA Typing Techniques*, p. 194-205 (1993).
Illmensee, K. and Mintz, B., "Totipotency and normal differentiation of single teratocarcinoma cells cloned by injection into blastocysts", *Proc. Natl. Acad. Sci. USA* 73(2): 549-53 (1976).
Ingram, M. et al., "Three-Dimensional Growth Patterns of Various Human Tumor Cell Lines in Simulated Microgravity of a NASA Bioreactor", *In Vitro Cell. Dev. Biol. Animal* 33:459-66 (1997).
Jacobson, L., et al., "Differentiation of Endoderm Derivatives, Pancreas and Intestine, From Rhesus Embryonic Stem Cells", *Transplantation Proceedings* 33:674 (2001).
Johe, K.K., et al., "Single factors direct the differentiation of stem cells from the fetal and adult central nervous system", *Genes Dev* 10(24): 3129-40 (1996).
Jones,.H. W., et al., "A technique for the aspiration of oocytes from human ovarian follicles", *Fertility and Sterility* 37(1):26-29 (1982).
Kaufman M.H., et al., "*Establishment of pluripotential cell lines from haploid mouse embryos,*"J. Embryol. Exp. Morphol., 73:249-61 (1983).
Kaiser-McCaw, B., et al., "Ovarian teratomas: cytologic data", *Cytogenet Cell Genet* 16: 391-95 (1976).
Keefer, C. L., et al., "Bovine Inner Cell Mass Cells as Donor Nuclei in the Production of Nuclear Transfer Embryos and Calves", *Biology of Reproduction* 50:935-39 (1994).
Kehat, I., et al., "Human embryonic stem cells can differentiate into myocytes with structural and functional properties of cardiomyocytes", *The Journal of Clinical Investigation* 108: 407-14 (2001).

Keil, F., et al., "Effect of interleukin-3, stem cell factor and granulocyte-macrophage colony-stimulating factor on committed stem cells, long-term culture initiating cells and bone marrow stroma in a one-step long-term bone barrow culture", *Ann Hematol* 79(5): 243-48 (2000).
Keller, G., et al., "Hematopoietic Commitment during Embryonic Stem Cell Differentiation in Culture", *Molecular and Cellular Biology* 13: 473-86 (1993).
Kim, H., et al., "The Expression of Peroxisome Proliferator-Activated Receptor $\gamma$ in Pig Fetal Tissue and Primary Stromal-Vascular Cultures", *Obes Res* 8(1): 83-88 (2000).
Lanza, R.P., et al., "Encapsulated celll technology", *Nature Biotechnology* 14(9): 1107-11 (1996).
Lee, S., et al., "Efficient generation of midbrain and hindbrain neurons from mouse embryonic stem cells", *Nature Biotechnology* 18: 675-78 (2000).
Lee et al., "Allelic discrimination by nick-translation PCR with fluorogenic probes", *Nucleic Acids Res.* 21:3761-3766, 1993.
Lieschke, G.J. and Dunn, A. R., "Development of functional macrophages from embryonal stem cells in vitro", *Experimental Hematology* 23: 328-34 (1995).
Linder, D., and Power, J., "Further evidence for post-meiotic origin of teratomas in the human female", *Ann. Hum. Genet.* 34: 21-30 (1970).
Linder, D., et al., "Origin of extragonadal teratomas and endodermal sinus tumours", Nature 254: 597-98 (1975).
Linder, D., "Gene Loss in Human Teratomas", *P.N.A.S*63: 699-704 (1969).
Lisek E. W. and Levine, L. A., et al., "Percutaneous Technique for Aspiration of Sperm from the Epididymis and Testicle", *Techniques in Urology* 3(2): 81-85 (1997).
Liu, S., et al., "Embryonic stem cells differentiate into oligodendrocytes and myelinate in culture and after spinal cord transplantation", *PNAS*97(11):6126-31 (2000).
Lopez-Fernandez, J., et al., "Differentiation of Lactotrope Precursor GHFT Cells in Response to Fibroblast Growth Factor-2", *The J. Bio. Chem.* 275(28): 21653-60 (2000).
Lumelsky, N. et al., "Differentiation of Embryonic Stem Cells to Insulin-Secreting Structures Similar to Pancreatic Islets", *Science* 292: 1389-94 (2001).
Mann, J.R., "Properties of androgenetic and parthenogentic mouse embryonic stem cell lines; are genetic imprints conserved", *Developmental Biology* 3: 77-85 (1992).
Martin et al., "Characterization of 12 microsatellite loci of the human MHC in a panel of reference cell lines", Immunogenetics 47:131-138, (1998).
Matthews, J.A., et al., "Analytical Strategies for the Use of DNA Probes", Anal. Biochem., 169, 1-25, 1988.
Maxam et. al., "A New Method for Sequencing DNA", Proc. Natl. Acad. Sci. USA 74:560-564, 1977.
McDonald, J.W., et al., "Transplanted embryonic stem cells survive, differentiate and promote recovery in injured rat spinal cord", *Nature Medicine* 5:1410-12 (1999).
McKarney, L. A., et al., "Myogenesis in cultures of uniparental mouse embryonic stem cells: differing patterns of expression of myogenic regulatory factors", *Int J. Dev. Biol.* 41(3): 485-90 (1997).
Mori, M., et al., "*HLA gene and haplotype frequencies in the North American population: the National Marrow Donor Program Donor Registry,*" Transplantation, 64(7):1017-27 (1997).
Mountford, P., et al., "Maintenance of pluripotenial embryonic stem cells by stem cell selection", *Reprod. Fertil. Dev.* 10:527-33 (1998).

Muller, M., et al., "Selection of ventricular-like cardiomyocytes from ES cells in vitro", *The FASEB J.* 14: 2540-48 (2000).

Mullis, K.B. et al., "Specific Synthesis of DNA in Vitro via a Polymerase-Catalyzed Chain Reaction," Methods Enzymol. 155:335-350 (1987).

Nakano, T., et al., "Generation of Lymphohematopoietic Cells from Embryonic Stem Cells in Culture", *Science* 265: 1098-1101 (1994).

Nakayama, N. et al, "Natural Killer and B-Lymphoid Potential in CD34+Cells Derived From Embryonic Stem Cells Differentiated in the Presence of Vascular Endothelial Growth Factor", *Blood* 91: 2283-95 (1998).

Newton et al., "Analysis of any point mutation in DNA. The amplification refractory mutation system", Nucleic Acids Res. 17:2503-2516, 1989.

Nicolas, J.F., et al., "Cell Lines Derived from Teratocarcinomas", *Cancer Research* 36: 4224-31 (1976).

Nikiforov et al., "Genetic Bit Analysis: a solid phase method for typing single nucleotide polymorphisms", Nucletic Acids Res. 22:4167-4175, 1994.

Nogues, C., et al., "Ultrastructural studies of early mouse embryos obtained by oocyte fusion", Zygote 2(1): 15-28 (1994).

Okabe, S., et al., "Development of neuronal precursor cells and functional postmitotic neurons from embryonic stem cells in vitro", *Mechanisms of Development* 59:89-102 (1996).

Olson et al., "A Common Language for Physical Mapping of the Human Genome", Science 245:1434-1435, 1989.

Orita et al., "Rapid and Sensitive Detection of Point Mutations and DNA Polymorphisms Using the Polymerase Chain Reaction", Genomics 5:874-879 (1989).

Palacios, R., et al., "In vitro generation of hematopoietic stem cells from an embryonic stem cell line", *Proc. Natl. Acad. Sci. USA* 92:7530-34 (1995).

Park, J., et al., "Differentiative potential of a mouse parthenogenetic embryonic stem cell line revealed by embryoid body formation in vitro", *Jpn. J. Vet. Res.* 46(1): 19-28 (1998).

Parrington, J. M., et al., "The origin of ovarian teratomas", *Journal of Medicinal Genetics* 21: 4-12 (1984).

Pera, M. F. and Herzfeld, D., "Differentiation of human pluripotent teratocarcinoma stem cells induced by bone morphogenetic protein-2", *Reprod. Feri. Dev.* 80: 551-55 (1998).

Pirastu et al., "Prenatal Diagnosis of β-Thalassemia", New England J. Med. 309:284-287, 1983.

Potocnik, A. J., et al., "Reconstitution of B cell subsets in Rag deficient mice by transplantation of in vitro differentiated embryonic stem cells", *Immunology Letters* 57: 131-37 (1997).

Przyborski, S. A., et al., "Developmental regulation of neurogenesis in the pluripotent human embryonal carcinoma cell line NTERA-2", *European Journal of Neuroscience* 12: 3521-28 (2000).

Ramiya, V. K., et al., "Reversal of insulin-dependent diabetes using islets generated in vitro from pancreatic stem cells", *Nature Medicine* 6(3):278-82 (2000).

Rogers, M. B., et al., "Bone Morphogenetic Proteins-2 and -4 are Involved in the Retinoic Acid-Induced Differentiation of Embryonal Carcinoma Cells", *Molecular Biology of the Cell* 3: 189-96 (1992).

Saiki et al., "Enzymatic Amplification of β-Globin Genomic Sequences and Restriction Site Analysis for Diagnosis of Sickle Cell Anemia", *Science*, 230, 1350-1354 (1985).

Saito, S., et al., "Bovine embryonic stem cell-like cell lines cultured over several passages", *Roux's Arch. Dev. Biol.* 201: 134-41 (1992).

Sanger et. al, "DNA Sequencing with Chain-terminating inhibitors", Proc. Natl. Acad. Sci. USA 74 5463-5467, 1977.

Schuldiner, M., et al., "Effects of eight growth factors on the differentiation of cells derived from human embryonic stem cells", *PNAS* 97(21): 11307-12 (2000).

Sekirina, G.G., *Ontogenez.* 16(6):583-8 (1985).

Serup, P., "Panning for pancreatic stem cells", *Nature Genetics* 25: 134-135 (2000).

Sheldon et al., "Matrix DNA Hybridization", Clin. Chem. 39(4):718-719 1993.

Sims, J. E., et al., "Interleukin 1 signaling occurs exclusively via the type 1 receptor", *P.N.A.S. USA* 90:6155-59 (1993).

Stanford, W. L., et al., "Expression Trapping: Identification of Novel Genes Expressed in Hematopoietic and Endothelial Lineages by Gene Trapping in ES Cells", *Blood* 92: 4622-31 (1998).

Stewart, C. L., et al., "Rapid Communication: Stem Cells from Primordial Germ Cells Can Reenter the Germ Line", *Developmental Biology* 161: 626-28 (1994).

Stice, S. L., et al., "Bovine Nuclear Transfer Embryos: Oocyte Activation Prior to Blastomere Fusion", *Mol Reprod Dev* 38(1): 61-68 (1994).

Surani, M. A., et al., "Genome imprinting and development in the mouse", *Development 1990 Supplement:* 89-98, 1990 Supp.

Surti, U., et al., "Genetics and Biology of Human Ovarian Teratomas. I. Cytogenetic Analysis and Mechanism of Orgin", *Am J Hum Gene* 47: 635-43 (1990).

Suzuki, A. and Nakano, T., "Development of Hematopoietic Cells From Embryonic Stem Cells", *International Journal of Hematology* 73: 1-5 (2001).

Syvanen, A.C., "Nucleic Acid Hybridization: From research tool to routine diagnostic method", Medical Biology, 64, 313-324 1986.

Tada, T., et al., "Epigenotype switching of imprintable loci in embryonic germ cells", *Dev Genes Evol* 207:551-61 (1998).

Takeuchi, T., et al., "A reliable technique of nuclear transplantation for immature mammalian oocytes", *Human Reproduction* 14(5): 1312-17 (1999).

Tanksley S. et al, "RFLP Mapping In Plant Breeding: New Tools For An Old Science", *Biotechnology* 7:257-264 (1989).

Taylor, A.S., et al., "The early development and DNA content of activated human oocytes and parthenogenetic human embryos", Hum. Reprod., 9(12):2389-97 (1994).

Taylor, G., et al., "Involvement of Follicular Stem Cells in Forming Not Only the Follicle but Also the Epidermis", *Cell* 102: 451-61(2000).

Thomson, J. A., et al., "Pluripotent Cell Lines Derived from Common Marmoset (Callithrix jacchus) Blastocysts", *Biol. Reprod.* 55: 254-59 (1996).

Thomson, J. A., et al., "Embryonic Stem Cell Lines Derived from Human Blastocysts", *Science* 282: 1145-47 (1998).

Thomson, J. A., et al., "Isolation of a primate embryonic stem cell line", *P.N.A.S USA* 92: 7844-48 (1995).

Trounson, A., "Nuclear transfer in human medicine and animal breeding", *Reprod. Fertil. Dev.* 13: 31-39 (2001).

Van Stekelenburgh-Hamers, A. E. P., et al., "Isolation and Characterization of Permanent Cell Lines From Inner Cell Mass Cells of Bovine Blastocysts", *Molecular Reproduction and Development* 40: 444-54 (1995).

Van T'Hof, R., et al., "Stem cell factor stimulates chicken osteoclast activity in vitro", *FASEB J* 11(4):287-93 (1997).

Vortmeyer, A. O., et al., "Microdissection-Based Analysis of Mature Ovarian Teratoma", *American Journal of Pathology* 154: 987-91 (1999).

Vos et al., "AFLP: a new technique for DNA fingerprinting", Nucleic Acids Res. 23:4407-4414, 1995.

Wallace et al., "Hybridization of synthetic oligodeoxyribonucleotides to Φx174 DNA: the effect of single base pair mismatch", Nucleic Acids Res. 6:3543-3557, 1979.

Weber, J. L. et al., "Abundant Class of Human DNA Polymorphisms Which Can Be Typed Using the Polymerase Chain Reaction," Am. J. Hum. Genet. 44:388-396 (1989).

Wheeler, M. B. "Development and Validation of Swine Embryonic Stem Cells: a Review", *Reprod. Fertil. Dev.* 6: 563-68 (1994).

Wiles, M. V. and Keller, G., "Multiple hematopoietic lineages develop from embryonic stem (ES) cells in culture", *Development* 111:259-67 (1991).

Williams et al., "DNA polymorphisms amplified by arbitrary primers are useful as genetic markers", Nucleic Acids Res. 18:6531-6535 (1990).

Wobus, A. M., et al., "Embryonic Stem Cells and Nuclear Transfer Strategies", *Cells Tissues Organs* 166: 1-5 (2000).

Wobus, A. M., et al., "Differentiation-promoting effects of mammary-derived growth inhibitor (MDGI) on pluripotent mouse embryonic stem cells", *Virchows Archiv B Cell Pathol* 59:339-42 (1990).

Woodbury, D., et al., "Adult Rat and Human Bone Marrow Stromal Cells Differentiate Into Neurons", *Journal of Neuroscience Research* 61: 364-70 (2000).

Wolosin, J. M., et al., "Stem Cells and Differentiation Stages in the Limbo-corneal Epithelium", *Progress in Retinal and Eye Research* 19(2):223-55 (2000).

Zandstra, P. W., et al., "A ligand-receptor signaling threshold model of stem cell differentiation control: a biologically conserved mechanism applicable to hematopoiesis", *Blood* 96(4): 1215-22 (2000).

* cited by examiner

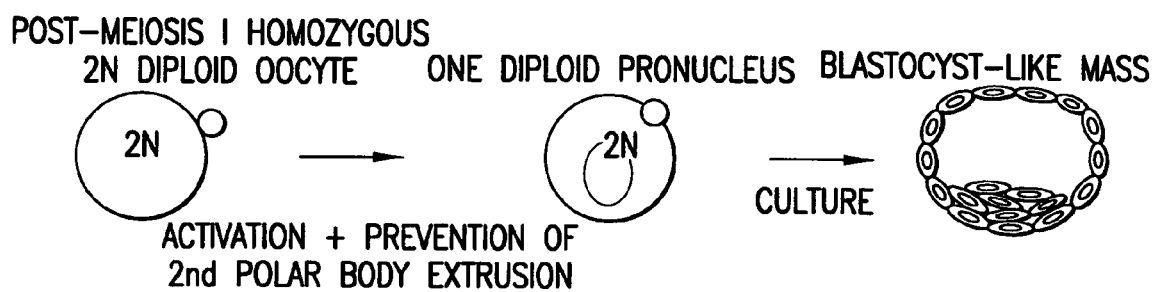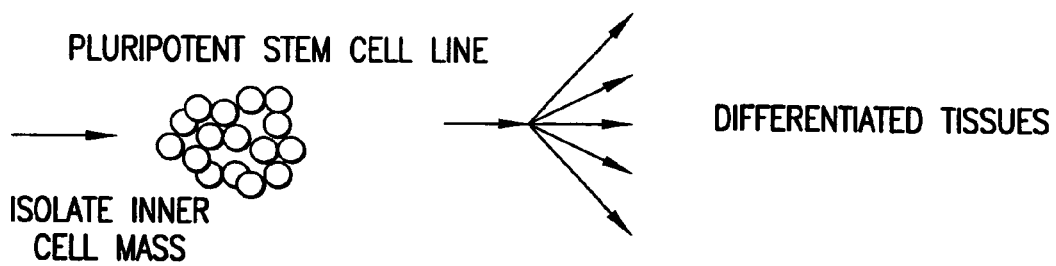
FIG.2

Serological Specificities of the HLA-A, -B, and -C Loci

| A locus | B locus | | C locus |
|---|---|---|---|
| A1[a] | B5 | B50(21)[a] | Cw1[a] |
| A2[a] | B7[a] | B51(5)[a] | Cw2[a] |
| A203 | B703 | B5102 | Cw3[a] |
| A210 | B8[a] | B5103 | Cw4[a] |
| A3[a] | B12 | B52(5)[a] | Cw5[a] |
| A9 | B13[a] | B53[a] | Cw6[a] |
| A10 | B14[a] | B54(22) | Cw7[a] |
| A11[a] | B15 | B55(22)[a] | Cw8[a] |
| A19 | B16 | B56(22)[a] | Cw9(w3) |
| A23(9)[a] | B17 | B57(17)[a] | Cw10(w3) |
| A24(9)[a] | B18[a] | B58(17)[a] | |
| A2403 | B21 | B59 | |
| A25(10)[a] | B22 | B60(40)[a] | |
| A26(10)[a] | B27[a] | B61(40)[a] | |
| A28 | B35[a] | B62(15)[a] | |
| A29(19)[a] | B37[a] | B63(15)[a] | |
| A30(19)[a] | B38(16)[a] | B64(14)[a] | |
| A31(19)[a] | B39(16)[a] | B65(14)[a] | |
| A32(19)[a] | B3901(16) | B67 | |
| A33(19)[a] | B3902(16) | B70[a] | |
| A34(10)[a] | B40 | B71(70)[a] | |
| A36 | B4005 | B72(70)[a] | |
| A43 | B41[a] | B73 | |
| A66 | B42[a] | B75(15) | |
| A68(28)[a] | B44(12)[a] | B76(15) | |
| A69(28)[a] | B45(12)[a] | B77(15) | |
| A74(19) | B46 | B7801 | |
| | B47[a] | Bw4[a] | |
| | B48 | Bw6[a] | |
| | B49(21)[a] | | |

[a] Serological specificities to be included in a screening panel.

FIG.4A

Officially Recognized HLA-DR and HLA-DQ.
Specificities 1992[3]

DR1
DR103
DR2
DR3
DR4
DR5
DR6
DR7
DR8
DR9
DR10
DR11(5)
DR12(5)
DR13(6)
DR14(6)
DR1403
DR1404
DR15(2)
DR16(2)
DR17(3)
DR18(3)
DR51
DR52
DR53

DQ1
DQ2
DQ3
DQ4
DQ5(1)
DQ6(1)
DQ7(3)
DQ8(3)

(N) = the broad HLA-DR or HLA-DQ specificity

FIG.4B

Restriction Endonucleases for Genotyping of DQA1, DQB1, DRB1, DRB3, DRB5, DPA1, and DPB1 Alleles

| Allele | Antigen | Restriction endonucleases |
|---|---|---|
| DQA1 | | ApaLI, HphI, BsaJI, FokI, MboII, MnlI |
| DQB1 | DQw1 | FokI, ApaI, HaeII, SfaNI, BssHII, HphI |
| | DQw2,3,4 | FokI, BglI, SacI, AcyI, HpaII |
| DRB1 | DR1 | AvaII, PstI |
| | DR2 | FokI, Cfr13I, HphI |
| | DR3,5,6,8 | AvaII, FokI, KpnI, HaeII, Cfr13I, SfaNI, SacII, BsaJI, ApaI, HphI, RsaI |
| | DR4 | SacII, AvaII, HinfI, HaeII, HphI, MnlI |
| DRB3 | | HinfI, KpnI, HphI |
| DRB5 | | SfaNI, Cfr13I |
| DPA1 | | AluI, AcyI, MboII |
| DPB1 | | Bsp1286I, FokI, DdeI, BsaJI, BssHII, Cfr13I, RsaI, EcoNI, AvaII |

FIG.5

List of SSOs for HLA Class II Oligotyping

SSO Probes for HLA-DR Generic Typing

| | Oligo seq 5' - 3' | AA | Specificity |
|---|---|---|---|
| L11 | TTCAAACTTAAGCTGCCAC | 9-14 | DR1 |
| D11 | CTCATACTTATCCTGCTGC | 9-14 | DR2 |
| N77 | TCTGCAGTAGTTGTCCACC | 75-80 | DR3 |
| H33 | CTCTTGGTGATAGAAGTATC | 29-53 | DR4 |
| E58 | CCAGTACTCCTCATCAGGC | 56-61 | DR11 |
| L37 | AGCGCAGGAGCTCCTCCTG | 34-39 | DR12 |
| G11 | CTTATACTTACCCTGCCAC | 9-14 | DR7 |
| L74 | GTGTCCACCAGGGCCCGCC | 71-77 | DR5 (+1403) |
| Y26 | CTGTGCAGATACCGCACCC | 23-29 | DR9 |
| V11 | CTCAAACTTAACCTCCTCC | 9-14 | DR10 |
| E71 | GGCCCGCTGCTGTCTTCCAGG | 68-73 | DR13 (1301, 1302, 1304) |
| | | | DR1 (0103) |
| | | | DR4 (0402, 0414) |
| | | | DR11 (1102, 03) |
| K71 | CGGCCCGCTTGTCTTCCAG | 68-73 | DR13-HAG (1303) |
| H60 | GTTCCAGTGCTCCGCAGCA | 57-62 | DR14 (1401, 04, 07) |
| N37 | AGCGCACGTTCTCCTCCTG | 34-39 | DR3 |
| | | | DR13 (1301, 02, 04, 06) |
| | | | DR14 (1402, 03, 06) |
| D37 | GAAGGCGAAGTCCTCCTCT | 34-40 | DR2 (DRB5*0101) |
| AV86 | GCTCTCCACAGCCCCGTAG | 83-88 | DR2 (DRB5*02) |
| | | | DR1 (0102) |
| | | | DR12 |

FIG.6A

SSO Probes for the Analysis of DRB1, DRB3, DRB5 Subtypes

| Oligo | seq 5' - 3' | AA | Specificity |
|---|---|---|---|
| G13 | ACACTCACCGTAGAGTAC | 9-14 | 0801-0805, 1105, 1201, 1202, 1404 |
| H30-2 | ATAGAAGTGTCTGTCCAGG | 27-32 | 1503 |
| N37 | AGCGCACGTTCTCCTCCTG | 34-39 | 0301, -02, 1301, 1302, 1305, 1306, 1402, 1403, 1406 |
| S37 | AGCGCACGGACTCCTCTTG | 34-39 | 0406 |
| S57 | GCCTAGCGCGAGTACTG | 56-61 | 0405, 0409 - 0412, 0801, 0803, 0805, 1303, 1304 |
| H60 | GTTCCAGTGCTCCGCAGCA | 57-62 | 1401, 1404, 1407 |
| F67 | CTTCCAGGAAGTCCTTCTG | 64-69 | 1601, 1101, 1103 - 1105, 1202, 1305 |
| I67 | CTTCCAGGATGTCCTTCTG | 64-69 | 0803, 1102, 1201, 1301 - 1304, 1306, 0412 |
| I67-2 | ACATCCTGGAAGACGAGC | 66-71 | 0103, 0402, 0414, 1102, 1301, 1302, 1304 |
| E71 | GGCCCGCTCGTCTTCCAGG | 68-73 | 0103, 0402, 0414, 1102, 1103, 1301, 1302, 1304 |
| K71 | | 68-73 | 1303 |
| QK71 | CGGCCCGCTTGTCTTCCAG | 68-73 | 0401, 0413 |
| QR71 | CCGGGCCCGCCCTTGCTC | 69-74 | 0404, 0405, 0408, 0410 - 0411 |
| QR71-2 | CGGCCCGCCTCTGCTCCAG | 68-73 | 0101, 0102, 0403 - 0408, 0410, 0411, 1402, 1406 |
| R71 | GGCCCGCTGTCTTCCAGG | 68-73 | 1101, 1104, 1105, 1305, 1306, 0801 - 0805, 1403, 0412 |
| R71-2 | CCGCGGCGCCTGTCTTC | 69-74 | 1601, 1602, DRB5*0101, 0102 |
| RR71 | AGCGGAGGCGGGCCGAGG | 69-74 | 1401, 1404, 1405, 1407 (DRB*0101) |
| E74 | GTGTCCACCTTGGCCCGCC | 71-77 | 0403, 0406, 0411, 1404, 1405, 1407 |
| L74 | GTGTCCACCAGGGCCCGCC | 71-77 | 0801 - 0805, 1403, 0412 |
| V86 | AACTACGGGGTTGTGGAG | 82-87 | Val86 |
| G86 | AACTACGGGGTTGGTGAG | 82-87 | Gly86 |
| AV86 | GCTCTCCACAGCCCGTAG | 83-88 | 0102, 1201, 1202 DRB5*02 |

FIG.6B

| Locus | 5' Primer sequence | 3' Primer sequence |
|---|---|---|
| D6S276 | 5-tcaatcaaatcatccccagaag | 5-ccttctttgcagactgtcacc |
| D6S105 | 5-gggattacaggcaggagccac | 5-gaaggagaattgtaatttccg |
| MOGCA | 5-gaaatgtgagaataaaggaga | 5-gataaagggaactactaca |
| D6S265 | 5-agtcaccctactgtgctatc | 5-atcgaggtaaacagcagaaag |
| MIB | 5-gcttcacccgatcagtagaagac | 5-gcatggtgtcagagatagtcaggtc |
| D6S275 | 5-ggagaagttgagtatttcctgc | 5-accaaacttcaaattttcgg |
| DQCAR11 | 5-gcactatcattaaatttgcttttccacagtac | 5-tgattcataaggcaagaatccagcatattgg |
| DQCAR | 5-gaaacatatattaacagagacagacaaa | 5-catttctcttccttatcacttcata |
| G51152 | 5-ggtaaaattcctgactgcc | 5-gacagctcttcttaacctgc |
| TAP1CA | 5-gctttgatctcccctc | 5-ggacaatatttttgctcctgagg |
| RING3CA | 5-tgcttataggagactaccg | 5-gagtaatgtcacaggatggg |
| D6S291 | 5-ggcattcaggcatgcctggc | 5-ggggatgacgaattattcactaact |

FIG. 7

PCR Primers for Amplification of the DQA1, DQB1, DRB1, DRB3, DRB5, DPA1, and DPB1 Genes

| Gene | | Primers | Sequences (5' to 3') | | Den. | Ann. | Ext. |
|---|---|---|---|---|---|---|---|
| DQA1 | | 5'Primer GH26 | GTGCTGCAGGTGTAAACTTGTACCAG | (242 bp) | 94°C | 62°C | 72°C |
|  | | 3'Primer GH27 | CACGGATCCGGTAGCAGCGGTAGAGTTG | | | | |
| DQB1 | For DQw1 | 5'Primer GH28NL | GCATGTGCTACTTCACCAACG | (241 bp) | 94°C | 55°C | 72°C |
|  |  | 3'Primer QB202 | CACCTGCAGATCCCGGGTACGCCACCTC | | | | |
|  | For DQw2 DQw3 DQw4 | 5'Primer GH28NL | GCATGTGCTACTTCACCAACG | (237 bp) | 94°C | 55°C | 72°C |
|  |  | 3'Primer QB204 | CACCTGCAGTGCGGAGCTCCAACTGGTA | | | | |
| DRB1 | For DR2 | 5'Primer 5'R2 | TTCCTGTGGCAGCCTAAGAGG | (261 bp) | 94°C | 60°C | 72°C |
|  | For DR4 | 5'Primer 5'R4 | GTTTCTTGGAGCAGGTTAAAC | (263 bp) | 94°C | 60°C | 72°C |
|  | For DR9 | 5'Primer 5'R9-1 | GAAGCAGGATAAGTTTGAGTG | (256 bp) | 94°C | 55°C | 72°C |
|  | For DR1 | 5'Primer 5'R1 | GGTTGCTGGAAAGATGCATCT | (206 bp) | 94°C | 55°C | 72°C |
|  | For DR7 | 5'Primer 5'R7 | AGTTCCTGGAAAGACTCTTCT | (206 bp) | 94°C | 60°C | 72°C |
|  | For DR10 | 5'Primer 5'R10 | GGTTGCTGGAAAGACGCGTCC | (206 bp) | 94°C | 60°C | 72°C |
|  | For DR3 DR5 DR6 DR8 | 5'Primer 5'R3568 | ACGTTTCTTGGAGTACTCTACG | (265 bp) | 94°C | 60°C | 72°C |
|  |  | 3'Primer 3'R (common for DRB1) | CCGCTGCACTGTGAAGCTCT | | | | |
| DRB3 | | 5'Primer DRBAMP-52 | CCCAGCACGTTTCTTGGAGCT | (271 bp) | 94°C | 60°C | 72°C |
|  | | 3'Primer 3'R | CCGCTGCACTGTGAAGCTCT | | | | |
| DRB5 | | 5'Primer 5'DRB5 | CTTGCAGCAGGATAAGTAT | (259 bp) | 94°C | 60°C | 72°C |
|  | | 3'Primer 3'R | CCGCTGCACTGTGAAGCTCT | | | | |
| DPA1 | For 3rd exon | 5'Primer PL | GGAAGCTTGATCCCCAGTGCTGAGGTGACCG | (288 bp) | 92°C | 58°C | 72°C |
|  |  | 3'Primer PR | GGGGATCTTGAGGCTTGAGGAGGAGCGGC | | | | |
|  | For TM exon | 5'Primer PLTM | GGAAGCTTGAGGCCCAAGAGCCAATCCA | (161 bp) | | | |
|  |  | 3'Primer PRTM | GGGGATCCGCCAGAACGCAGAGACTT | | | | |
| DPB1 | | 5'Primer DPB101N | GTGAAGCTTTCCCGCAGAGAATTAC | (299 bp) | 94°C | 62°C | 72°C |
|  | | 3'Primer DPB201 | CACCTGCAGTCACTCACCTCGGCGCTG | | | | |

Note: Den.: Denature, Ann.: annealing, Ext.: extention.

FIG.11

SEQUENCE LISTING

<160> NUMBER OF SEQ ID NOS: 86

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 1
ttcaaactta agctgccac                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 2
ctcatactta tcctgctgc                                                  19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 3
tctgcagtag ttgtccacc                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 4
ctcttggtga tagaagtatc                                                 20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 5
ccagtactcc tcatcaggc                                                  19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 6

-continued agcgcaggag ctcctcctg                                                19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 7
cttatactta ccctgccac                                                19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 8
gtgtccacca gggcccgcc                                                19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 9
ctgtgcagat accgcaccc                                                19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 10
ctcaaactta acctcctcc                                                19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 11
ggcccgctcg tcttccagg                                                19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 12
cggcccgctt gtcttccag                                                19

<210> SEQ ID NO 13
<211> LENGTH: 19
<212> TYPE: DNA
<213> ORGANISM: Artificial Sequence

```
<220> FEATURE:
<223> OTHER INFORMATION: Description of Artificial Sequence: Probe

<400> SEQUENCE: 13
gttccagtgc tccgcagca                                                    19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 14
agcgcacgtt ctcctcctg                                                    19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 15
gaagcgcaag tcctcctct                                                    19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 16
gctctccaca gccccgtag                                                    19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 17
acactcaccc gtagagtac                                                    19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 18
atagaagtgt ctgtccagg                                                    19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 19
agcgcacgtt ctcctcctg                                                    19
```

```
<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 20
agcgcacgga ctcctcttg                                              19

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 21
gcctagcgcc gagtactg                                               18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 22
gttccagtgc tccgcagca                                              19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 23
cttccaggaa gtccttctg                                              19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 24
cttccaggat gtccttctg                                              19

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 25
acatcctgga agacgagc                                               18

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Probe
```

<400> SEQUENCE: 26
ggcccgctcg tcttccagg                                                19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 27
cggcccgctt gtcttccag                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 28
cggcccgctt ctgctcgac                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 29
ccgcggcccg cctctgctc                                                19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 30
cggcccgcct ctgctccag                                                19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 31
ggcccgcctg tcttccagg                                                19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 32
ccgcggcgcg cctgtcttc                                                19

<210> SEQ ID NO 33

```
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 33
agcggaggcg ggccgagg                                              18

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 34
gtgtccacct cggcccgcc                                             19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 35
gtgtccacca gggcccgcc                                             19

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 36
aactacgggg ttgtggag                                              18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 37
aactacgggg ttggtgag                                              18

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 38
gctctccaca gccccgtag                                             19

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 39
```
tcaatcaaat catccccaga ag                                    22

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 40
gggattacag gcaggagcca c                                     21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 41
gaaatgtgag aataaaggag a                                     21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 42 agtcaccta ctgtgctatc                                        20

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 43
gcttcacccg atcagtagaa gac                                   23

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 44
ggagaagttg agtatttctg c                                     21

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 45
gcactatcat taaatttgct ttccacagta c                          31

<210> SEQ ID NO 46
<211> LENGTH: 28
<212> TYPE: DNA

```
<213> ORGANISM: Artificial Sequence
<220> FEATURE:
<223> OTHER INFORMATION: Description of Artificial Sequence: Primer

<400> SEQUENCE: 46
gaaacatata ttaacagaga cagacaaa                                           28

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
ggtaaaattc ctgactggcc                                                    20

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 48
gctttgatct cccccctc                                                      18

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 49
tgcttatagg gagactaccg                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 50
ggcattcagg catgcctggc                                                    20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 51
ccttctttgc agactgtcac c                                                  21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 52
gaaggagaat tgtaattccg                                                    20
```

```
<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 53
gataaagggg aactactaca                                              20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 54
atcgaggtaa acagcagaaa g                                            21

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 55
gcatggtgtc agagatagtc aggtc                                        25

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 56
accaaacttc aaattttcgg                                              20

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 57
tgattcataa ggcaagaatc cagcatattg g                                 31

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 58
catttctctt ccttatcact tcata                                        25

<210> SEQ ID NO 59
<211> LENGTH: 20
<212> TYPE: DNA
<213> ORGANISM: Artificial Sequence
<220> FEATURE:
```

-continued

<223> OTHER INFORMATION: Description of Artificial Sequence: Primer

<400> SEQUENCE: 59
gacagctctt cttaacctgc                                           20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 60
ggacaatatt ttgctcctga gg                                        22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 61
gaggtaatgt cacaggatgg g                                         21

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 62
ggggatgacg aattattcac taact                                     25

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 63
gtgctgcagg tgtaaacttg taccag                                    26

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 64
cacggatccg gtagcagcgg tagagttg                                  28

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 65
gcatgtgcta cttcaccaac g                                         21

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 66
cacctgcaga tcccgcggta cgccacctc                                    29

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 67
gcatgtgcta cttcaccaac g                                            21

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 68
cacctgcagt gcggagctcc aactggta                                     28

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 69
ttcctgtggc agcctaagag g                                            21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 70
gtttcttgga gcaggttaaa c                                            21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 71
gaagcaggat aagtttgagt g                                            21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Primer

```
<400> SEQUENCE: 72
ggttgctgga aagatgcatc t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 73
agttcctgga aagactcttc t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 74
ggttgctgga aagacgcgtc c                                              21

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 75
acgtttcttg gagtactcta cg                                             22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 76
ccgctgcact gtgaagctct                                                20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 77
cccagcacgt ttcttggagc t                                              21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 78
ccgctgcact gtgaagctct                                                20

<210> SEQ ID NO 79
<211> LENGTH: 19
```

```
<212> TYPE: DNA
<213> ORGANISM: Artificial Sequence
<220> FEATURE:
<223> OTHER INFORMATION: Description of Artificial Sequence: Primer

<400> SEQUENCE: 79
cttgcagcag gataagtat                                            19

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 80
ccgctgcact gtgaagctct                                           20

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 81
ggaagcttga tccccctgag gtgaccg                                   27

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 82
ggggatcccc agtgcttgag gagcggc                                   27

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 83
ggaagcttga ggcccaagag ccaatcca                                  28

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 84
ggggatccgc cagaacgcag agactt                                    26

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 85
```

-continued

```
gtgaagcttt ccccgcagag aattac                                    26
```

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 86

```
cacctgcagt cactcacctc ggcgctg                                   27
```

US 7,030,292 B2

METHOD FOR PRODUCING A POPULATION OF HOMOZYGOUS STEM CELLS HAVING A PRE-SELECTED IMMUNOTYPE AND/OR GENOTYPE, CELLS SUITABLE FOR TRANSPLANT DERIVED THEREFROM, AND MATERIALS AND METHODS USING SAME

The present application claims the benefit of U.S. Provisional Application Ser. No. 60/258,881, filed, Jan. 2, 2001.

I. FIELD OF THE INVENTION

The present invention relates to methods of producing a homogenous population of homozygous stem (HS) cells pre-selected for immunotype and/or genotype from donor homozygous post-meiosis I diploid germ cells. The invention further relates to methods of using such histocompatible HS cells for diagnosis, therapeutic and cosmetic transplantation, cell replacement and/or gene therapy, and the treatment of various genetic diseases, neurodegenerative diseases, traumatic injuries, and cancer.

The invention further relates to methods for using histocompatible HS cells pre-selected for a non-disease genotype for prophylactic and therapeutic intervention including, but not limited to, diagnosis, therapeutic and cosmetic transplantation (including, but not limited to, skin grafts for wound and bum repair, replacement bone, cartilage and tendon for use in reconstruction of broken limbs, and repair of ears, noses, lips, and scalp), cell replacement and/or gene therapy, and the treatment of various genetic diseases including, but not limited to, neurodegenerative diseases, traumatic injuries, and cancer.

Furthermore, the invention relates to methods for differentiating genotyped and/or HLA-typed ("immunotyped") HS cells to create progenitor cells, and other differentiated cells, masses of cells or tissue types.

Finally, the invention relates to methods for providing catalogued transplant depository for HS cell lines from multiple donors, each HS cell line being homozygous for a unique HLA haploytpe, and histocompatible with any individual carrying the HLA components of such haplotype for the purpose of having a constant, reliable, comprehensive supply of cells for diagnosis, treatment and/or transplantation.

Moreover, the methods described in the present application are useful in combination with materials and methods disclosed in U.S. Patent Application Ser. No. 09/997,240, entitled "Isolated Homozygous Stem Cells, Differentiated Cells Derived Therefrom, and Methods of Making and Using Same," filed Nov. 30, 2001, that claims the benefit of U.S. Provisional Application Ser. No. 60/253,943, filed Nov. 30, 2000, both of which are incorporated by reference herein.

II. BACKGROUND OF THE INVENTION

Tissue transplants from one individual to another are at risk of rejection. The degree of risk is proportional to the degree of disparity between certain genetic products, antigens, expressed on the surface of donor and recipient cells. To ensure the success of a transplant, donor tissue must be immunohistologically compatible with recipient tissue, that is, donor and recipient tissue must be matched. Matching is accomplished when donor tissue expresses "self" antigens. T-cells from the recipient will then recognize donor tissue as "self", and will not form an immune response against it.

In all mammalian species studied, there is a single genetic locus that encodes the strongest transplantation antigens. This is known as the major histocompatibility complex (MHC). Human leukocyte antigen (HLA) is the genetic designation for the human counterpart to the MHC. HLA restricts, and therefore regulates, the immune response in a highly specific way. Molecules encoded by HLA bind and present foreign microbial antigens to an individual's own T-cells. In fact, foreign antigens can only be recognized by the T-cells of an individual if they are presented in the context of the individual's own HLA molecules. Therefore, HLA molecules participate in a trimolecular complex comprised of the T-cell receptor, the foreign microbial antigen, and the self-HLA molecule.

In the context of transplants, donor tissue expressing non-self HLA antigens is reliably killed by cytotoxic T-cells. Tissue grafts can be rejected on the basis of HLA molecules that differ from self-HLA molecules by as little as one amino acid. It is believed that the main reason for such rejection is that non-self HLA molecules recognize and form complexes with many peptides not recognized by self-HLA molecules. T-cells are intolerant of these non-self HLA-peptide complexes, and possibly bind to distinctive features of the non-self HLA molecule.

Therefore, matching donor and recipient tissue for HLA reduces the chances of a cytotoxic T-cell response in the recipient, and thus raises the chances of survival of a transplant. However, matching itself presents a problem for transplantation. First, there are two classes of HLA molecules, class I and II. Second, there are several genes for each HLA class, and each of these genes has many alleles (i.e. HLA is polymorphic). While HLA provides an individual with the capability of a diverse immune response, it makes transplantation from one individual to another a difficult task because it makes donor-recipient matching difficult to achieve.

In humans, there are three genes for class I HLA molecules, HLA-A, HLA-B, and HLA-Cw, and three genes for class II HLA molecules, HLA-DR, -DP, and -DQ. Furthermore, HLA genes are polymorphic. There are 22 different HLA-A alleles, 42 different -B alleles, 9 different -Cw alleles, and 18 different -DR alleles. Adding to the complexity of matching, an individual has two of each A, B, Cw, and DR alleles, where one set of A, B, Cw, and DR (a haplotype) is inherited from each parent, therefore individuals may be homozygyous or heterozygous for the A, B, Cw, and DR haplotypes.

Currently, transplantation using HLA-A, -B, -Cw, and -DR matched unrelated donor tissue makes enormous demands on tissue typing resources. This is largely due to the polymorphic nature of the HLA genes, and the need for high stringency of matching to minimize rejection and acute graft vs. host disease. On average, due to HLA polymorphism, the chance of finding a donor-recipient match for HLA-A, -B, -Cw, and -DR would range from one in 1,000 to one in several million depending on the frequency of the patient's tissue type in the general population. See also, Hansen, J. A., Anasetti, C., Peterdorf, E., Clift, R. A. and Martin, P. J., "*Marrow tranplants from unrelated donors*," Transplant Proc., 1994 June 26:1719–1712 (Review).

The present invention provides a reliable source of cells or tissue carrying two sets of identical HLA haplotypes, that significantly increases the possibility of a histological match between a donor and recipient, and hence, may be used for diagnosis, transplant and/or treatment. HS cells are homozygous and express only one HLA haplotype. Thus, a donor HS cell has only one HLA haplotype to be matched with the recipient instead of two, as in heterozygous stem cells. HS cells can be taken from random donors of multiple ethnicities to provide a depository or bank of HS cell populations that immunohistologically match at least one haplotype carried by individuals in the population at large. The depository needs only contain about 200 different HS cell lines, each having a distinct HLA haplotype, to service most of the general population (i.e., provide immunohistocompatible cells suitable for transplant).

Further, gene therapy in humans raises ethical concerns. A distinction has been drawn between genetic manipulations that involve only somatic cells and manipulations that may involve germ cells. Somatic manipulations are generally allowed as they affect only the patient, whereas germ cell manipulations are disallowed as they affect the patient's progeny. Moreover, research in transgenic animals has demonstrated that gene defects can be effectively corrected only by genetic manipulations of embryos. However, this approach is not feasible for gene therapy in humans for practical reasons, for example the level of insertional mutagenesis caused by the integration of retroviral vectors into cellular DNA may be unacceptably high.

The present invention also promises significant advances in gene-replacement therapy. Currently, there are many obstacles to gene therapy. Concerns such as whether a disease is suitable for genetic intervention, whether the gene for the disorder has been identified and cloned, whether there is an efficient way of introducing a gene into cells, or whether the gene can be expressed in tissues other than the affected tissue to be efficacious, significantly impede the practicability of gene therapy.

Thus, there is clearly a need in the art for a reliable source of histocompatible cells or tissue, which may be used for transplant and/or treatment, including gene therapy. For example, HS cells that are histocompatible with a patient suffering from a genetic disease can be genetically manipulated before being differentiated into a particular cell type for transplant.

III. SUMMARY OF THE INVENTION

The present invention relates to isolated homozygous stem (HS) cells and the discovery that these cells may be selected for immunotype and genotype, therefore being useful for diagnosis, transplantation and/or treatment.

The present invention also provides a depository or bank for HS cell lines typed for HLA-A, -B, -Cw, and -DR by serological or molecular methods, which would reduce the demand on tissue typing resources. Additionally, the present invention provides cells selected for not just immunotype, but also genotype. Hence, it provides a method for treating genetic disorders for example by cell transplants, where HS cells pre-selected for a non-disease genotype may be transplanted to the affected area. Thus, effectively providing gene therapy without actual genetic intervention.

Furthermore, the invention disclosed herein provides methods for producing HLA-typed HS cells, and progenitor cells and differentiated cells derived therefrom. Hence, the present invention, is useful in combination with the teachings of U.S. patent application Ser. No. 09/997,240, entitled "Isolated Homozygous Stem Cells, Differentiated Cells Derived Therefrom, and Methods of Making and Using Same," filed Nov. 30, 2001, and U.S. Provisional Application Ser. No. 60/253,943, which provides pluripotent homozygous stem (HS) cells, methods and materials for making same, and methods for differentiating HS cells into progenitor cells or other desired differentiated cells, groups of cells or tissues in vivo or in vitro.

HS cells are created upon activation of non-fertilized post-meiosis I diploid germ cells from stemplasms when transplanted into a live animal. It is a further object to isolate HS cells from the various stages of development within said stemplasm. It is another object of the invention to provide methods of selecting the cells to be isolated from said stemplasm.

The HS cells of the present invention are pluripotent, and raise no ethical concerns as they are isolated from cell-masses that are non-fertilized and incapable of developing into viable embryos. Moreover, immunohistocompatibility matching is difficult to accomplish when heterozygous ES cell lines are employed in tissue or cell transplantation therapy, or maintained in banks and/or depositories. This is because the ES cell lines, including those developed by Advanced Cell Technology and other organizations, are derived from fertilized embryos or from nuclear transfer techniques using adult differentiated cells, and are genomically heterozygous (e.g., WO 01/84920A1, WO 01/79445A2 and WO 01/29206A1). Because the pluripotent stem cells of the present invention, being derived from post-meiosis I germ cells, or stemplasms, are genomically homozygous (with minimal heterozygosity or uniform homozygosity) or are selected for MHC homozygosity (as in the cases of the fusion and nuclear transfer of two haploid germ cells), such cells may be used to overcome immunohistocompatibility problems faced by currently available transplantation, cell replacement, and gene therapy techniques employing ES cell lines, or maintaining ES cell line banks and/or depositories.

During gametogenesis, heterozygous germ cells, i.e. germ cells with both paternal and maternal chromosomes, undergo meiosis. In the first meiotic division (meiosis I), homologous chromosomes separate to form two homozygous daughter cells that contain either paternal or maternal chromosomes with some heterozygosity introduced because of the phenomenon of crossing-over. Further, during oogenesis, the extrusion of one daughter cell (the primary polar body) is observed. The other daughter cell is arrested at metaphase II. Such metaphase II diploid oocytes may be used to derive homozygous stem cells with minimal heterozygosity.

Upon proper activation, a metaphase II oocyte can proceed to complete meiosis by the extrusion of one chromatid (i.e. the secondary polar body) and give rise to a haploid cell. Such meiosis-completed haploid oocyte self-replicates without cytokinesis, rendering it diploid and uniformly homozygous. Such meiosis-completed haploid oocytes, hence, may also be used to create the homozygous stem cells of the present invention with no heterozygosity. See also, Kaufman M. H., Robertson E. J., Handyside A. H., Evans M. J., "*Establishment of pluripotential cell lines from haploid mouse embryos*," J. Embryol. Exp. Morphol., 73:249–61 (1983). Stem cells derived from stemplasms derived from post-meiosis I or II germ cells also carry the above mentioned homozygosity. Stem cells derived from the fusion or nuclear transfer of two haploid germ cells from an individual can have a larger degree of heterozygosity, nevertheless those homozygous for MHC can be selected and used in cell based therapeutic applications.

Both HS cells with minimal heterozygosity and uniform homozygosity are superior to stem cells with heterozygous ES cells (such as those derived from using fertilized embryos, nuclear transfer, therapeutic cloning embryos, and adult stem cells) in that homozygous stem cells can contain two sets of identical Major Histocompatibility Complex (MHC) haplotypes. Therefore, immunohistocompatibility matching between a donor and an individual in need of transplantation therapy is easier to achieve with HS cells. Such stem cells homozygous for one MHC haplotype are tolerated not only by recipients carrying the identical haplotype, but also by recipients with the same MHC components in either of their parental haplotypes.

Human MHC loci are within 4 Mb on chromosome 6, and MHC alleles are usually inherited en bloc. Some MHC allelic combinations are shared in a considerably higher frequency in the population, for example the 15 most common HLA-A, -B, -Cw, -DR haplotypes are shared by 21.3% Caucasian Americans, and similar observations of haplotype frequency are seen in other ethnical backgrounds. Furthermore, common HLA haplotypes in one racial group are shared significantly by other groups. For example, 156 haplotypes of the 184 common haplotypes in Caucasian Americans are shared at least once by African Americans, Asian Americans, Latin Americans, or Native Americans. The number of common haplotypes of other racial groups and the corresponding number of shared haplotypes are: African Americans (198/63); Asian Americans (210/100); Latin Americans (194/147); and Native Americans (194/173). Mori, M., et al., "*HLA gene and haplotype frequencies in the North American population: the National Marrow Donor Program Donor Registry*," Transplantation, 64(7): 1017–27 (1997). Considering such evidence supporting such linkage disequilibrium, the use of non-fertilized post-meiosis I diploid gamete derived HS cells can reduce the number of immunologically different cell lines needed to be maintained in a stem cell bank or depository for tissue or cell transplantation.

Hence, potentially, a few hundred stem cell lines that are homozygous for different haplotypes will be sufficient to match a majority of the population. This number is tremendously smaller in contrast to the number of haplotypes needed to maintain a bank or depository for stem cell lines derived from embryonic stem cells, adult stem cells, or therapeutic cloning stem cells. For example, for every 200 haplotypes there are more than 20,000 heterozygous possibilities (FIG. 1).

The present invention when used in combination with the invention described in U.S. patent application Ser. No. 09/997,240, and U.S. Provisional Application Ser. No. 60/253,943, supra, is useful for, including, but not limited to, the diagnosis and treatment of various diseases, such as genetic diseases, neurodegenerative diseases, endocrine-related disorders and cancer, traumatic injuries, cosmetic and therapeutic transplantation, and gene therapy and cell replacement therapy.

The present invention provides a method of producing a population of homozygous stem cells that are selected for immunotype and/or genotype. HS cells are immunotyped for HLA-A, -B, -Cw, and -DR using serological and/or molecular techniques known in the art. HS cells are further selected for genotype using molecular techniques known in the art. Such HS cells may be then be used to derive progenitor cells, and/or other differentiated cells, groups of cells or tissue types using methods disclosed in U.S. patent application Ser. No. 07/997,240, and U.S. Provisional Application Ser. No. 60/253,943, incorporated by reference herein. Additionally, the present invention provides methods for using pre-HLA typed HS-derived differentiated cells and/or tissues for therapeutic or cosmetic transplantation, and/or treatment of genetic and neurodegenerative disorders, traumatic injuries and cancer.

It is an object of the invention to provide a method for producing a population of homozygous stem cells from mitotically activated homozygous post-meiosis I diploid germ cells having a target immunotype such that they are suitable for transplant into an intended recipient by, (a) assaying the immunotype, that is, the homozygous or heterozygous HLA haplotype, of the intended recipient to determine the target immunotype, (b) producing mitotically activated post-meiosis 1 diploid germ cell samples to give rise to multiple blastocyst-like masses, each of which contains an inner cell mass (ICM) homozygous for a particular HLA haplotype, (c) assaying the immunotype of each said ICM so as to select one carrying the target HLA haplotype, and (d) culturing HS cells isolated from the selected ICM to create permanent HS cell lines homozygous for the target HLA haplotype. It is a further object of the invention to provide HS cells derived from the intended recipient, or a close relative of the intended recipient or person unrelated to the intended recipient carrying at least one HLA haplotype common to the intended recipient. Known techniques are used for assaying and harvesting HS cells carrying the target HLA haplotype, and assaying the immunotype of the intended recipient and donor.

As described in detail in U.S. patent application Ser. No. 09/997,240, and U.S. Provisional Application Ser. No. 60/253,943, which are incorporated by reference herein, HS cells are derived from a blastocyst-like mass that is created by: (a) fusing two oocytes or two spermatids; (b) preventing the extrusion of the second polar body during oogenesis; (c) allowing the extrusion of the second polar body and spontaneous genomic self-replication in appropriate conditions; or, (d) transferring two haploid egg or sperm nuclei into an enucleated oocyte, where methods (a) and (d) require the additional for screening for homozygous stem cells by genotyping.

It is another object of the present invention to provide a method of isolating a population of recipient histocompatible homozygous stem cells from stemplasms created by the process described in detail in U.S. patent application Ser. No. 09/997,240 and U.S. Provisional Application Ser. No. 60/253,943, which are incorporated by reference herein. Such a population of recipient histocompatible, HS cells would be created by, (a) assaying the immunotype and genotype of the intended recipient to determine the target immunotype and genotype; (b) mitotically activating donor homozygous post-meiosis I diploid germ cells to develop multiple blastocyst-like masses, each of which contains an inner cell mass (ICM) that is homozygous for a particular allele; (c) isolating HS cells from the selected ICM, and culturing said HS cells to create cell lines; (d) assaying the genotype of each said HS cell line, and selecting one that is homozygous for the target genotype. Said HS cells may be identified from the stemplasm created after implantation through histological means and assayed for proper HLA haplotype and genotype.

It is another object of the present invention to provide a method for producing a population of recipient histocompatible, homozygous stem cells from mitotically activated homozygous post-meiosis I diploid germ cells having a target genotype, that is, the non-disease allele of the target gene, such that they are suitable for transplant into an intended recipient by: (a) assaying the genotype and HLA-haplotype of the intended recipient to determine the target immunotype and genotype; (b) mitotically activating donor homozygous post-meiosis I diploid germ cells to develop multiple blastocyst-like masses, each of which contains an inner cell mass (ICM) that is homozygous for a particular allele, and a particular HLA haplotype; (c) isolating HS cells from the said ICM, and culturing said HS cells to create cell lines; and (d) assaying the HLA haplotype and genotype of each said HS cell line and selecting one carrying the target HLA haplotype and genotype.

It is a further object of the invention to provide HS cells derived from the intended recipient carrying one functional allele, or a close relative of the intended recipient or person unrelated to the intended recipient carrying at least one HLA haplotype common to the intended recipient, and at least one non-disease allele of the target gene. Known techniques are used for assaying and harvesting HS cells carrying the target HLA haplotype and the target genotype, and assaying the immunotype and genotype of the intended recipient and donor.

It is another object of the invention to provide methods for making a desired cell, group of cells, or tissue type which comprises directing the differentiation of an isolated, immunotyped, and/or genotyped HS cell, under suitable conditions using factors in vivo or in vitro, so as to arrive at the desired cell, group of cells, or tissue type. Exemplary tissues include, but are not limited to, epithelial tissues, connective tissue, muscle tissue or nervous tissue.

Illustrative types of epithelial cells include, but are not limited to, keratinizing epithelial cells; wet-stratified barrier epithelia; lining epithelial cells; exocrine-secreting epithelial cells; endocrine-secreting epithelial cells; extracellular matrix-secreting epithelial cells; absorptive epithelial cells, such as those of the gut, exocrine glands, and urogenital tract; and contractile epithelial cells. Illustrative types of connective tissue cells include, but are not limited to, extracellular matrix-secreting cells; cells specialized for metabolism and storage; and circulating cells of the blood and immune systems. Illustrative types of muscle cells include, but are not limited to, contractile cells and ciliated cells with propulsive function. Illustrative types of nervous or sensory cells include, but are not limited to, sensory transducers; autonomic neurons; supporting cells of sense organs and of peripheral neurons; and neurons and glial cells of the central nervous system. Illustrative types of reproductive cells include, but are not limited to, germ cells and nurse cells.

It is another object of the invention to provide a catalogued transplant depository or bank containing populations of pre-HLA-typed HS cells derived from multiple donors, each population homozygous for at least one HLA haplotype, so as to have a reliable, constant, comprehensive supply of immunohistocompatible cells for diagnosis transplantation and/or treatment.

It is another object of the invention to provide a method of treating a disorder or disease state in an individual by generating, in situ or in vitro, suitable replacement cells, groups of cells, tissues or organs from isolated HS cells that are immunohistologically compatible with said individual. Illustrative disorders and disease states include, but are not limited to, traumatic injury (e.g., post-trauma repair and reconstruction, limb replacement, spinal cord injury, burns, and the like) and birth defects; pathological and malignant conditions of the cells, tissues, and organs (e.g., cancer); and degenerative and congenital diseases of the cells and tissues of the muscles (e.g., cystic fibrosis, muscular dystrophy, cardiac conditions), nerves (e.g., Alzheimer's, Parkinson's, and multiple sclerosis), epithelium (e.g., blindness and myopathy, atherosclerosis and other stenotic vascular conditions, enzyme deficiencies such as Crohn's disease, and hormone deficiencies such as diabetes), and connective tissues (e.g., immune conditions and anemia). HS-derived cells and tissues may be grafted or transplanted to a subject in need, preferably using the subject's own donor material.

These and further objects of the invention are fully described by the below detailed description, examples, and claims, although none is a limitation of the scope of the invention.

IV. BRIEF DESCRIPTION OF THE FIGURES

The patent or application file contains at least one drawing executed in color. Copies of this patent or patent application publication with color drawings will be provided by the Office upon request and payment of the necessary fee.

FIG. 1: Graph depicting the difference in the quantity of cells needed for a non-HS cell bank versus a HS cell bank.

FIG. 2: Schematic diagram illustrating the derivation of HS cells from post-meiosis I oocytes.

Figure 3:
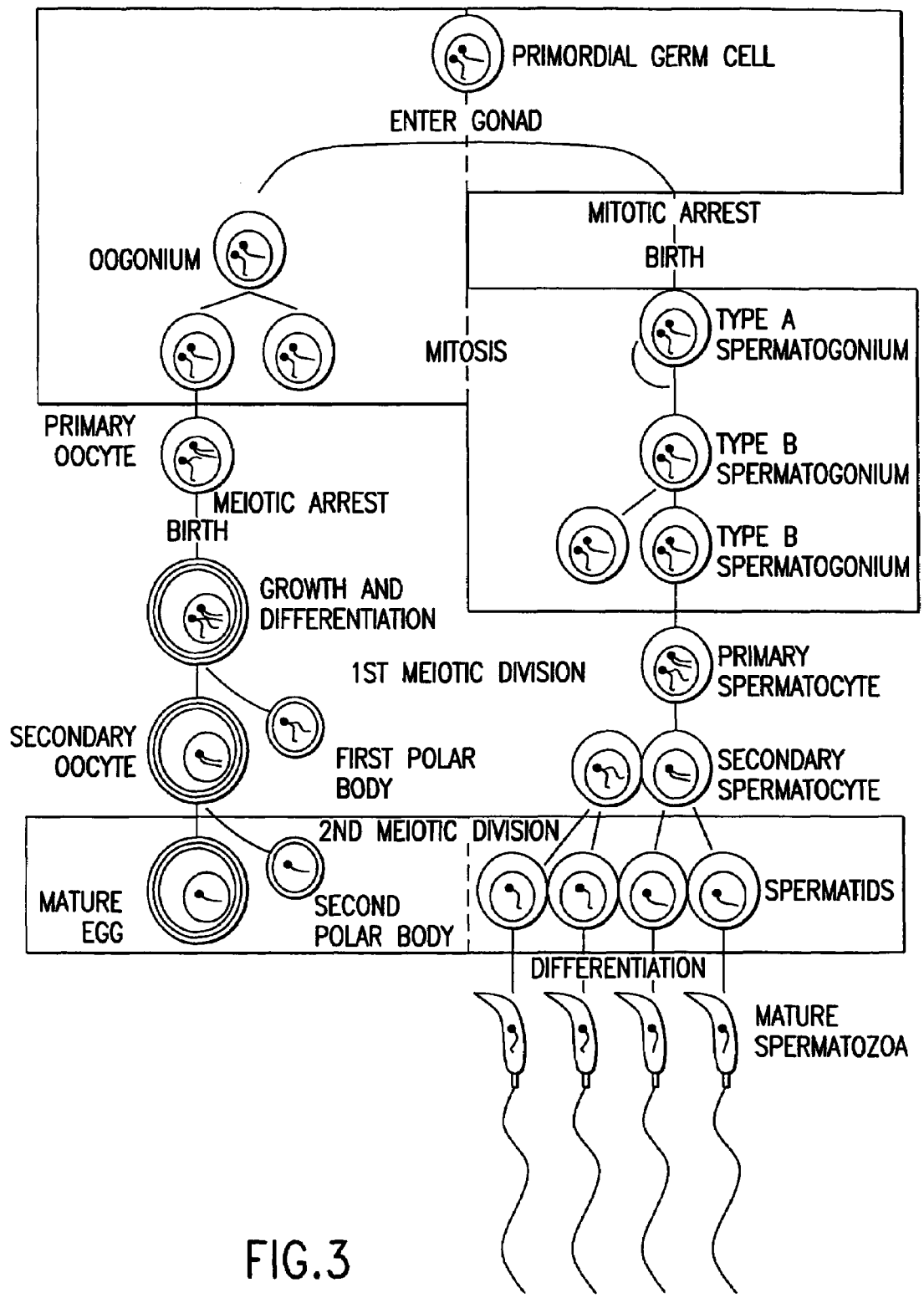

FIG. 3: Schematic representation of spermatogenesis and oogenesis

FIG. 4A: Table showing serological specificities of HLA loci

FIG. 4B: Officially recognized HLA-DR and HLA-DQ Specificities

FIG. 5: A list of exemplary restriction endonucleases for genotyping of HLA class II alleles FIG. 6: A list of exemplary SSO probes for HLA class II typing SSO Probe List:
  SSO Probe L11 (SEQ ID NO. 1)
  SSO Probe D11 (SEQ ID NO. 2)
  SSO Probe N77 (SEQ ID NO. 3)
  SSO Probe H33 (SEQ ID NO. 4)
  SSO Probe E58 (SEQ ID NO. 5)
  SSO Probe L37 (SEQ ID NO. 6)
  SSO Probe G11 (SEQ ID NO. 7)
  SSO Probe L74 (SEQ ID NO. 8)
  SSO Probe Y26 (SEQ ID NO. 9)
  SSO Probe V11 (SEQ ID NO. 10)
  SSO Probe E71 (SEQ ID NO. 11)
  SSO Probe K71 (SEQ ID NO. 12)
  SSO Probe H60 (SEQ ID NO. 13)
  SSO Probe N37 (SEQ ID NO. 14)
  SSO Probe D37 (SEQ ID NO. 15)
  SSO Probe AV86 (SEQ ID NO. 16)
  SSO Probe G13 (SEQ ID NO. 17)
  SSO Probe H30-2 (SEQ ID NO. 18)
  SSO Probe N37 (SEQ ID NO. 19)
  SSO Probe S37 (SEQ ID NO. 20)
  SSO Probe S57 (SEQ ID NO. 21)
  SSO Probe H60 (SEQ ID NO. 22)
  SSO Probe F67 (SEQ ID NO. 23)
  SSO Probe I67 (SEQ ID NO. 24)
  SSO Probe I67-2 (SEQ ID NO. 25)
  SSO Probe E71 (SEQ ID NO. 26)
  SSO Probe K71 (SEQ ID NO. 27)
  SSO Probe QK71 (SEQ ID NO. 28)
  SSO Probe QR71 (SEQ ID NO. 29)
  SSO Probe QR71-2 (SEQ ID NO. 30)
  SSO Probe R71 (SEQ ID NO. 31)
  SSO Probe R71-2 (SEQ ID NO. 32)
  SSO Probe RR71 (SEQ ID NO. 33)
  SSO Probe E74 (SEQ ID NO. 34)
  SSO Probe L74 (SEQ ID NO. 35)
  SSO Probe V86 (SEQ ID NO. 36)
  SSO Probe G86 (SEQ ID NO. 37)
  SSO Probe AV86 (SEQ ID NO. 38)

FIG. 7: A list of exemplary sequences of primers used for microsatellite typing and sequencing Primer List:
  D6S276 5' Primer (SEQ ID NO. 39)
  D6S105 5' Primer (SEQ ID NO. 40)
  MOGCA 5' Primer (SEQ ID NO. 41)
  D6S265 5' Primer (SEQ ID NO. 42)
  MIB 5' Primer (SEQ ID NO. 43)
  D6S275 5' Primer (SEQ ID NO. 44)
  DQCAR11 5' Primer (SEQ ID NO. 45)
  DQCAR 5' Primer (SEQ ID NO. 46)
  G51152 5' Primer (SEQ ID NO. 47)
  TAP1CA 5' Primer (SEQ ID NO. 48)
  RING3CA 5' Primer (SEQ ID NO. 49)
  D6S291 5' Primer (SEQ ID NO. 50)
  D6S276 3' Primer (SEQ ID NO. 51)
  D6S105 3' Primer (SEQ ID NO. 52)
  MOGCA 3' Primer (SEQ ID NO. 53)
  D6S265 3' Primer (SEQ ID NO. 54)
  MIB 3' Primer (SEQ ID NO. 55)
  D6S275 3' Primer (SEQ ID NO. 56)
  DQCAR11 3' Primer (SEQ ID NO. 57)
  DQCAR 3' Primer (SEQ ID NO. 58)
  G51152 3' Primer (SEQ ID NO. 59)
  TAP1CA 3' Primer (SEQ ID NO. 60)
  RING3CA 3' Primer (SEQ ID NO. 61)
  D6S291 3' Primer (SEQ ID NO. 62)

Figure 8:
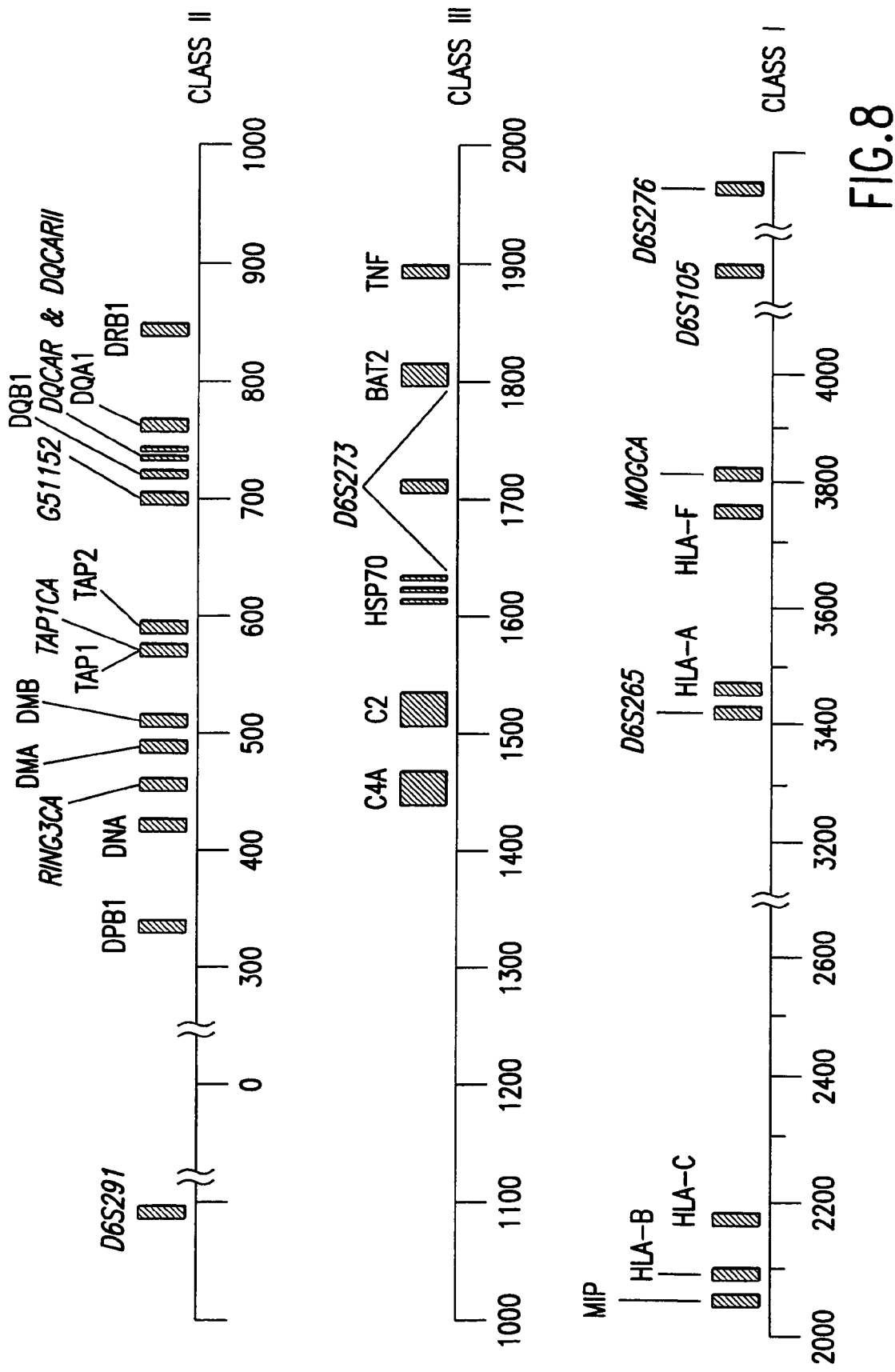
Figure 9A:
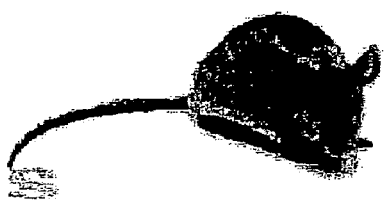
Figure 9B:
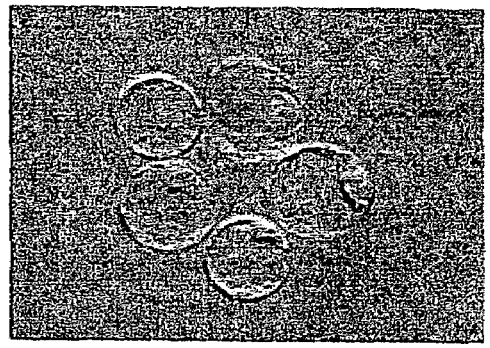
Figure 9C:
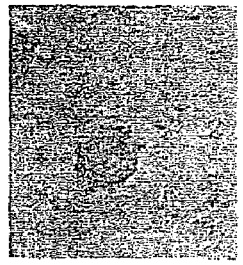
Figure 9D:
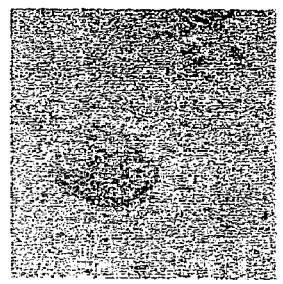
Figure 9E:
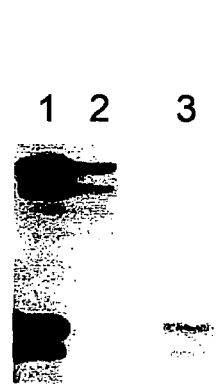
Figure 9F:
Figure 10A:
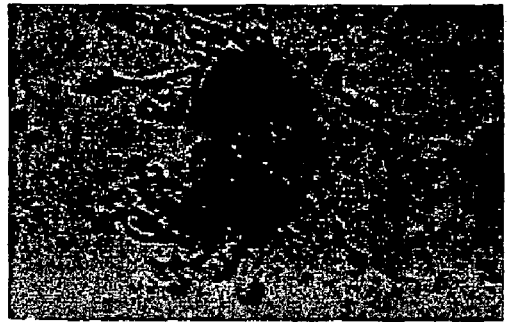

FIG. 8: Map of HLA class I, II, and III regions showing the relative location of the twelve microsatellites FIG. 9A: C57/DBA2 mouse FIG. 9B: Superovulated oocytes-derived blastocysts-like masses FIG. 9C: Representative colony I FIG. 9D: Representative colony II FIG. 9E: Results of genotyping experiment FIG. 9F: Results immunotyping experiment FIG. 10A: Photo of an isolated inner cell mass growing on feeder layers derived from mouse HS cells.

Figure 10B:

FIG. 10B: Photo depicting the development of a morula-like mass derived from human homozygous post-meiosis I diploid oocytes.

Figure 10C:

FIG. 10C: Photo of an early blastocyst-like mass derived from human homozygous post-meiosis I diploid oocytes.

Figure 10D:

FIG. 10D: Photo of a blastocyst-like mass revealing the inner cell mass derived from human homozygous post-meiosis I diploid oocytes.

FIG. 11: An exemplary list of PCR primers for amplification of HLA class II alleles Primer List:
  Gene DQA1, 5' Primer GH26 (SEQ ID NO. 63)
  Gene DQA1, 3' Primer GH27 (SEQ ID NO. 64)
  Gene DQB1 5' Primer GH28NL (SEQ ID NO. 65)
  Gene DQB1 3' Primer QB202 (SEQ ID NO. 66)
  Gene DQB1 5' Primer GH28NL (SEQ ID NO. 67)
  Gene DQB1 3' Primer QB204 (SEQ ID NO. 68)
  Gene DRB1 5' Primer 5' R2 (SEQ ID NO. 69)
  Gene DRB1 5' Primer 5' R4 (SEQ ID NO. 70)
  Gene DRB1 5' Primer 5' R9-1 (SEQ ID NO. 71)
  Gene DRB1 5' Primer 5' R1 (SEQ ID NO. 72)
  Gene DRB1 5' Primer 5' R7 (SEQ ID NO. 73)
  Gene DRB1 5' Primer 5' R10 (SEQ ID NO. 74)
  Gene DRB1 5' Primer 5' R3568 (SEQ ID NO. 75)
  Gene DRB1 3' Primer 3' R (SEQ ID NO. 76)
  Gene DRB3 5' Primer DRBAMP-52 (SEQ ID NO. 77)
  Gene DRB3 3' Primer 3' R (SEQ ID NO. 78)
  Gene DRB5 5' Primer 5' DRB5 (SEQ ID NO. 79)
  Gene DRB5 3' Primer 3' R (SEQ ID NO. 80)
  Gene DPA1 5' Primer PL (SEQ ID NO. 81)
  Gene DPA1 3' Primer PR (SEQ ID NO. 82)
  Gene DPA1 5' Primer PLTM (SEQ ID NO. 83)
  Gene DPA1 3' Primer PRTM (SEQ ID NO. 84)
  Gene DPB1 5' Primer DPB 101N (SEQ ID NO. 85)
  Gene DPB1 3' Primer DPB201 (SEQ ID NO. 86)

V. DETAILED DESCRIPTION AND PREFERRED EMBODIMENTS OF THE INVENTION

All references cited herein are hereby incorporated by reference in their entirety. Nothing herein is to be construed as an admission that the invention is not entitled to antedate such disclosure by virtue of prior invention. Throughout this description, the preferred embodiments and examples shown should be considered as exemplars, rather than as limitations on the present invention.

A. Definitions

In the context of the present invention, a HS cell system refers to stem cells derived from the blastocyst-like mass that results from the mitotic activation of an unfertilized homozygous post-meiosis I diploid germ cell, or from the fusion or nuclear transfer of two haploid germ cells, to stem cells derived from naturally occurring teratogenic tissues and to stem cells derived from stemplasms as described in U.S. patent application Ser. No. 09/997,240, and U.S. Provisional Patent Application Ser. No. 60/253,943, incorporated by reference herein. HS cells isolated from HS cell systems are pluripotent, and under appropriate conditions can be differentiated to produce multipotent progenitor cells, somatic cell precursors, and other types of differentiated cells.

"Differentiation" is a highly regulated process that cells undergo as they mature into normal functional cells. Differentiated cells have distinctive characteristics, perform specific functions and are less likely to divide. Conversely, undifferentiated cells are rapidly dividing immature, embryonic or primitive cells having a nonspecific appearance with multiple nonspecific activities and functions.

As used herein, the term "stem cell" refers to a relatively undifferentiated cell that actively divides and cycles, giving rise upon proper stimulation to a lineage of mature, differentiated, functional cells. The defining properties of a stem cell include: (a) it is not itself terminally differentiated; (b) it can divide without limit for the lifetime of the animal; and (c) when it divides, each daughter has a choice of remaining a stem cell or embarking on a course that leads irreversibly to terminal differentiation. Those stem cells that are initially unrestricted in their capabilities (i.e., capable of giving rise to several types of differentiated cell) are called "pluripotent". Current sources of pluripotent cells include embryonic (ES) stem cells, embryonic carcinoma (EC) cells, cells generated from somatic cloning, teratomas and teratocarcinomas.

Progenitor cell lines, each capable of producing cells from one of the three germ layers, i.e. the endoderm, mesoderm and ectoderm, are referred to in the present application as "multi-potent". While each progenitor cell line is not terminally differentiated and can continue to divide for the lifetime of an animal, it is considered to be committed to different tissues or cells from only one type of embryonic layer. Therefore, particular progenitor cell lines may be differentiated into bone, cartilage, smooth muscle, striated muscle and hematopoietic cells (mesoderm); liver, primitive gut, and respiratory epithelium (endoderm); or, neurons, glial cells, hair follicles and tooth buds (ectoderm). The term "progenitor cells" hence may be used synonymously with "multi-potent stem cells" or "precursor cells". Such progenitor cells lines, which are created by the directed differentiation of HS cells in vivo (where the term "in vivo" includes differentiation induced by encapsulating said HS cells in an immunocompromised animal to generate stemplasms from such encapsulated cells) or in vitro, can be maintained in culture as permanent cell lines.

A "teratoma" is a disorganized mass of cells containing many types of differentiated tissue, tissues derived from all three embryonic layers, such as bone, muscle, cartilage, nerve, tooth-buds, glandular epithelium, and so forth, mixed with undifferentiated stem cells that continually divide and generate yet more of these differentiated tissues.

A "teratocarcinoma" is secondary to a teratoma. Teratomas are largely benign; however if they become malignant, a teratocarcinoma develops and can be deadly to the host. Compared to other tumors, teratomas exhibit unique histological features. They are composed of various differentiated tissues, including tissues such as epidermis, central nervous system tissue, or mature cartilage. They also contain non-specific tissue types, e.g., lymphoid tissue or fibrous stroma.

A "stemplasm" is a newly derived term used to describe a mass that develops upon the transplantation of HS cells into a host. Unlike teratomas, a stemplasm exhibits controlled growth, while still containing cells from all three embryonic germ layers. It can therefore be used as a means for the in vivo differentiation of the HS cells of the present invention.

A "homozygous stem cell" is an undifferentiated stem cell arising from a nonfertilized post-meiosis I diploid germ cell. Preferably, it is formed by preventing the extrusion of the second polar body during oogenesis (or "activation"), or allowing the extrusion of the second polar body and spontaneous genomic self-replication of the haploid oocyte in appropriate conditions. Homozygous stem (HS) cells are isolated cells generated from the inner cell mass of blastocyst-like masses that develop upon "mitotic activation" of non-fertilized germ cells, which can be accomplished by: (a) fusing two oocytes or two spermatids; (b) preventing the extrusion of the second polar body during oogenesis; (c) allowing the extrusion of the second polar body and spontaneous genomic self-replication in appropriate conditions; or, (d) transferring two haploid egg or sperm nuclei into an enucleated oocyte.

In mammalian development, cleavage produces a thin-walled hollow sphere, the "blastocyst", with the embryo proper being represented by a mass of cells at one side, otherwise known as the "inner cell mass". The blastocyst is formed before implantation and is equivalent to the "blastula". The wall of the thin-walled hollow sphere is referred to as the "trophoblast", which is the extra-embryonic layer of epithelium that forms around the mammalian blastocyst, and attaches the embryo to the uterus wall. The trophoblast forms the outer layer of the chorion, and together with maternal tissue will form the placenta.

In the context of the present invention, a "blastocyst-like mass" is different from a "blastocyst" (as used in the art) in that it is the product of a mitotically activated nonfertilized post-meiosis I germ cells.

As used herein, the term "mitotically activated" means acquiring the ability to undergo regular cell divisions mitotically. Mitotic activation refers to the activation of germ cells so that meiosis II is either, (1) resumed and the haploid gamete cells, after self-replicating their genome without cytokinesis, then undergo mitotic division, or (2) resumed, but the haploid gamete cells are prevented from karyokinesis and cytokinesis, and then undergo mitotic division.

The term "homozygous post-meiosis I diploid germ cells", as used herein, means germ cells that are the stage of gametogenesis at which the cells contain two copies of either the paternal or maternal homologous chromosomes. And haploid germ cells means germ cells that have accomplished meiosis and carry only one copy of the chromosomes.

"Alleles" are alternative forms of a genetic locus. A single allele for each locus is inherited separately from each parent. In the context of the present invention, a cell is classified as "homozygous" if it contains two copies of the same allele. Conversely, a "heterozygous" cell contains two different alleles of the same genetic locus.

In the context of the present invention, an individual's "immunotype" is characterized by the unique array of proteins, known as histocompatibility antigens, disposed on the surface of a cell. In humans, these histocompatibility antigens are referred to as human leukocyte antigens or HLAs, a complex family of genetically inherited proteins found on the surface of cells throughout the body.

A primary determinant of a cell's immunotype is the HLA profile, a genetic fingerprint on white blood cells and platelets, composed of proteins that play a critical role in activating the body's immune system to respond to foreign organisms. The HLAs determine the match between an intended host and a potential donor in transplant procedures. Reactions to HLA antigens are the primary cause of tissue graft rejection. HLA factors are inherited from the mother and the father (one from each) so the greatest chance of having the same HLA type is between siblings (e.g., 1 in 4). Foreign cells having the same immunotype or HLA profile as those of a host's native cells will be accepted by the host as "self" and not rejected by the host's immune system.

HLA antigens are the products of multiple, closely linked genes on a single chromosome usually inherited as an intact unit. This histocompatibility complex, or HLA region, also contains genes important to complement and immune responses.

The HLA gene complex contains at least four loci known as HLA-A, -B, -Cw, and -DR. There are two classes of HLA antigens. Class I is comprised of HLA-A, -B, and -Cw. There are 22 different HLA-A antigens, 42 different -B antigens, 9 different -Cw antigens, and 18 different -DR antigens. HLA-A, -B, and -C antigens are expressed on nearly all human cells. An individual's class I HLA profile can be used to determine the degree of compatibility or genetic relationship between individuals, such as potential donors and recipients in transplantation of kidneys, bone marrow, etc., infusions of platelets or leukocytes, or for genealogical studies. Class I antigens may be identified by serologic methods. For example, an individual's Class I HLA profile may be determined by incubating sample lymphocytes with a battery of antisera having known specificities for certain A-, B-, or C-locus antigens. Positive cell/serum interactions characterize the HLA antigens of the cells.

Class II is comprised of HLA-DR and -DQ. There are 18 different DR antigens. These antigens are normally expressed on B lymphocytes, monocytes, macrophages, dendritic cells and endothelial cells, though they are induced on other cells by immune stimuli. Class II antigens (e.g. the DRβ1, DRβ3, DRβ4, DRβ5, and DQβ3 genes) can be detected by serologic and/or molecular analysis of patient DNA. If only mid-resolution typing is required, one may utilize Sequence Specific Oligonucleotide Probes (SSOP) for all regions of the gene. If high resolution (allelic level) is required, a combination of SSOP testing and DNA sequencing can be used. High resolution testing is usually performed only on bone marrow recipients and their prospective donors where a much greater degree of matching is essential.

Cells expressing one or more of the HLA proteins expressed by the host cells are perceived by the host's immune system as "self" whereas those expressing other HLA proteins are perceived as "foreign" or "non-self". The host's immune system gears up a response to the "foreign" or "non-self" proteins and kills off the foreign tissue. If the foreign tissue is a transplanted organ, this response is called rejection.

In the context of the present invention, donor cells are characterized "suitable for transplant" to an intended host if they may be stably grafted onto a host without rejection. To be suitable for transplant, donor cells must be "histocompatible" with the intended host, i.e., HLA "matched". If the HLA are substantially matched, the immune system is much less likely to respond. Humans inherit HLA proteins from their parents on the 6th chromosome. Since one gets two chromosome 6s (normally, one from the mother and one from the father), half of one's HLA proteins will match each of our parents. The more HLA proteins that match, the less likely a grafted organ will be rejected by the recipient.

An individual has two of each A, B, Cw, and DR alleles, where one set of A, B, Cw, and DR (a "haplotype") is inherited from each parent. Further, individuals may be homozygous or heterozygous for the A, B, Cw, and DR haplotypes. In the context of the present invention, a donor cell is considered to be HLA "matched" or "histocompatible" to an intended recipient, provided the donor cells do not express HLA products that are foreign to the recipient. For example, a donor cell that is homozygous for a haplotype such as HLA-A1, -Cw7, -B8 or HLA- A29, -Cw7, -B8, will match a recipient having a heterozygous HLA profile with both HLA-Al, -Cw7, -B8, and HLA-A29, -Cw8, -B65 haplotypes.

As used herein, the term "genotype" refers to the genetic constitution of an organism or a group of organisms. In the context of the present invention, the "target" genotype will be the normal or wild type sequence, i.e., that genetic sequence is not associated with a particular pathological condition. Such pathological conditions are often referred to as "genetic disorders", meaning they are linked to the expression of a mutant gene or genes. Genetic disorders often arise from specific gene mutations. In the context of the present invention, the genetic mutation linked to pathology can either be inherited (e.g., hereditary genetic disorders) or induced (e.g., exposure to carcinogens).

Exemplary inherited genetic disorders include but are not limited to Alzheimer's disease, diabetes, Graves disease, hemophilia, Huntington's disease, muscular dystrophy, Parkinson's disease, sickle cell anemia, and various metabolic disorders (i.e., enzyme deficiencies such as Phenylketonuria (PKU) and Severe Combined Immune Deficiency (SCID)). Exemplary induced genetic disorders include but are not limited to cancer and multiple sclerosis.

A catalog of genetic disorders and the human genes linked thereto is available through the Online Mendelian Inheritance in Man (Online Mendelian Inheritance in Man, OMIM (TM). McKusick-Nathans Institute for Genetic Medicine, Johns Hopkins University (Baltimore, Md.) and National Center for Biotechnology Information, National Library of Medicine (Bethesda, Md.), 2000. World Wide Web URL: http://www.ncbi.nlm.nih.gov/omim/). OMIM is a large searchable database of genetic diseases, disorders, and traits and their different manifestations maintained by the National Center for Biotechnology Information (NCBI). OMIM is available on the world wide web.

B. Creation of Homozygous Stem Cells of the Present Invention

As described in detail in U.S. application Ser. No. 09/997, 240, an HS cell is isolated from a blastocyst-like mass that develops upon the mitotic activation of a nonfertilized post-meiosis I diploid germ cell. FIG. 2 provides a flow chart, showing a preferred method of developing HS cells from a non-fertilized post-meiosis I diploid germ cell.

Germ cells develop into non-fertilized post-meiosis I diploid germ cells that, upon activation, produce blastocyst-like masses from which the HS cells of the present invention are derived. HS cells, and/or differentiated cells, of the present invention find utility in the diagnosis and/or treatment of diseases, include, but are not limited to implantation or transplantation to an affected individual in need of such therapy.

While homozygous post-meiosis I diploid germ cells may be obtained from the same individual or from an immuno-compatible donor, in certain situations self-donors are preferred. However, in cases where the affected individual selected for therapy suffers from a genetic disease (i.e., a disease characterized by a lack of a crucial gene, either due to mutation or improper expression), it may be preferable to utilize a non-self donor. Alternatively, one skilled in the art of selection procedures may choose those self germ cells that display the desired genotype (e.g., cells lacking a flawed or mutated gene), those cells capable of expressing the deficient gene. Such selection techniques may also be used to avoid an immuno-incompatible genotype or phenotype for tissue transplant.

HS cells homozygous for a HLA haplotype and a target gene can be derived and selected from: (a) fusing two oocytes or two spermatids; (b) preventing the extrusion of the second polar body during oogenesis; (c) allowing the extrusion of the second polar body and spontaneous genomic self-replication in appropriate conditions; or, (d) transferring two haploid egg or sperm nuclei into an enucleated oocyte. FIG. 3 provides a schematic representation of spermatogenesis and oogenesis, showing the difference in phases of mitosis and meiosis in males and females.

Oocytes useful in the context of the present invention may be obtained using any suitable method known in the art, or yet to be discovered. Human oocytes are typically harvested from the ovarian follicles of a donor individual and isolated from surrounding or adhering cells. To maximize yield, superovulation is induced in the donor individual. Superovulation may be induced by the administration of appropriate gonadotropins or gonadotropin analogues, administered either alone or in combination with clomiphene citrate (Barriere et al., Rev. Prat., 40(29):2689–93 (1990), incorporated by reference herein). In mice, an exemplary method involves the administration of pregnant mare's serum (PMS) to mimic follicle-stimulating hormone (FSH) and human chorionic gonadotropin (hCG) to mimic luteinizing hormone (LH). See Hogan et al., Manipulating the mouse embryo: A Laboratory Manual, $2^{nd}$ ed. Cold Spring Harbor Laboratory Press, 1994). Efficient induction of superovulation depends on several variables including, but not limited to, the age and weight of the female, the dose of gonadotropin, the time of administration, and the strain used.

Superinduction of ovulation and harvesting of oocytes are known in the art. For exemplary detailed mouse protocols, see Hogan et al., supra, pp. 130–132, the entire contents of which are hereby incorporated by reference. For example, Hogan describes the intraperitoneal administration of PMS and hCG, both resuspended from lyophilized powder in sterile 0.9% NaCl, to induce superovulation. Both PMS and hCG should be administered prior to the release of endogenous LH. The Hogan protocols, directed to the harvesting of oocytes from mice, can be routinely adapted for humans without undue experimentation.

Polyethylene glycol has also been shown to induce fusion of ovulated oocytes (see, e.g., Sekirina, G. G., Ontogenez. 16(6):583–8 (1985), and Gulyas, B. J., Dev. Biol. 101(1): 246–50 (1984), incorporated by reference herein). Alternatively, Nogues et al., Zygote, 2(1):15–28 (1994), (incorporated by reference herein) describes the induction of oocyte fusion by inactivated Sendai virus, resulting in the production of "zygotes" or "oocyte fusion products (OFP)" that are able to undergo the first stages of embryonic development. For a review of oocyte fusion techniques, see Gulyas, B. J., Dev. Biol., 4:57–80 (1986), incorporated by reference herein.

Alternatively, preventing the extrusion of the second polar body from oocytes can generate HS cells. A detailed protocol for activation of mouse oocytes is described in Hogan et al. supra, pp. 148–150, wherein harvested eggs with their cumulus cells attached are maintained in a solution of 7% ethanol in Dulbecco's PBS for 5 minutes, washed with medium, and incubated at 37° C. for 5 hours. The cumulus cells are subsequently removed by treatment with hyaluronidase. In nature, following the first meiotic division and separation of the first polar body, oocytes are arrested at metaphase II and can only undergo the second meiotic division when stimulated by a sperm. In vitro, the stimulation from the sperm can be mimicked by exposing oocytes to agents such as $Ca^{++}$ ionophore (A23187) or ethanol to trigger the continuation of meiosis II. Before the extrusion of the second polar body, karyokinesis (separation of chromosomes) and cytokinesis (division of cells) can be inhibited by agents including, but not limited to, 6-dimethylaminopurine (6-DMAP), or cytochalasin D, resulting in the activation of such diploid oocytes and subsequent formation of blastocyst-like masses. FIG. 2 depicts the products of activation.

In another embodiment, allowing the extrusion of the second polar body can be accomplished by exposing oocytes to $Ca^{++}$ ionophore (A23187) alone or followed by puromycin. The haploid oocytes can further undergo genomic self-replication without division, and the resulting diploid oocytes when incubated under appropriate conditions can form blastocyst like masses and may be used to derive HS cells. See, Taylor, A. S., et al., Hum. Reprod., 9(12):2389–97 (1994); and Kaufman, M. H. et al., J. Embryol. Exp. Morphol., 73:249–61 (1983).

Spermatids useful in the context of the present invention can be obtained using any suitable method known in the art or yet to be discovered, particularly those conventional in the field of in vitro fertilization. To create HS cells for use in a male, spermatids (meiosis II completed) are harvested and then induced to fuse. Spermatid fusion can be achieved using well-established standard techniques. For example, Asakura S, et al., Exp. Cell. Res., 181(2):566–73 (1989), incorporated by reference herein, teaches the use of a hypotonic medium to induce the fusion of a pair of spermatids and the eventual formation of a single acrosome (synacrosome). Alternately, secondary spermatocytes (meiosis I completed) can be activated using methods that are known in the art.

Homozygous post-meiosis I diploid germ cells can be harvested from a donor using conventional technology, particularly those techniques commonly used in the field of in vitro fertilization. See, for example, Jones et al., Fertil. Steril., 37(1):26–29 (1982), describing techniques for aspirating oocytes from human ovarian follicles; Lisek et al., Tech. Urol., 3(2):81–85 (1997), describing techniques for collecting sperm from the epididymis and testicle; Stice et al., Mol. Reprod. Dev., 38(1):61–8 (1994), and Takeuchi et al., Hum. Reprod., 14(5):1312–7 (1999), describing techniques for transplanting nuclear material of one donor to an enucleated oocyte of another. The entire contents of these references are hereby incorporated by reference herein.

Finally, as noted above, the isolated HS cell can be created from transferring two haploid germ cell nuclei to an enucleated oocyte. Specifically, two sperm or haploid egg nuclei can be transferred into an enucleated oocyte to create a non-fertilized diploid oocyte bearing the nuclear genetic information of the donor male or female in the oocyte cytoplasm. The donor nuclear material can be harvested and/or isolated using standard techniques conventional in the art. Likewise, the transfer step can be performed using techniques conventional in the art of in vitro fertilization (see U.S. Pat. No. 5,945,577, WO 98/07841, and see also, Stice and Takeuchi discussed above, as well as Wobus et al., Cells Tissues Organs, 166:1–5 (2000) incorporated by reference herein.

Genetic modifications may be introduced into HS cells by polynucleotide transfection techniques, including but not limited to, viral vector transfer, bacterial vector transfer, and synthetic vector transfer (e.g., via plasmids, liposomes and colloid complexes).

Methods for isolating ES cells from the inner cell mass of fertilized blastocysts are known in the art. Such methods may be adapted for isolating HS cells from the inner cell mass of blastocyst-like masses. For example, see Gardner et al., Curr. Op. Obst. Gyn., 11:307–311 (1999), U.S. Pat. No. 5,843,780 (Thomson et al.) and U.S. Pat. No. 5,905,042 (Stice et al.), the contents of which are incorporated by reference herein.

HS cells can be produced from any animal donor material and used in any animal system. Both human and non-human HS cells are contemplated by the present invention. Suitable veterinary applications include the generation of HS cells from and use in mammals, fish, reptiles, birds, and amphibians.

C. Method for Selecting Immunotype

Harvested homozygous post-meiosis I diploid germ cells, produced by the method noted above, are used to obtain HS cells and, ultimately, HS-derived progenitor cells, and other differentiated cells. The present invention encompasses further selecting HS cells for the immunotype and genotype of a target gene such that they may be used in the treatment of diseases, for example, by implantation or transplantation to an affected individual in need of such treatment.

Homozygous post-meiosis I diploid germ cells may be initially procured from an affected individual, in which case there would be no need for matching immunotype. However, in the case where such germ cells are taken from a donor who is related, or unrelated to the recipient, there is a need for selecting for immunotype. Furthermore, it is an object of the present invention to create a bank for stem cells that have been previously immunohistologically typed. In certain situations, a self-donor is preferred. However, in cases where an affected individual suffers from a genetic disease (i.e., a disease characterized by the lack of a crucial gene either due to mutation or improper expression), it may be preferable to utilize a non-self donor. Alternatively, it is another object of this invention that one skilled in the art of selection procedures may choose those self germ cells, which display the desired genotype (e.g., cells lacking a flawed or mutated gene), those cells capable of expressing the deficient gene. Such selection techniques may also be used to avoid an immuno-incompatible genotype or phenotype for tissue transplant.

The method for producing a homozygous population of cells suitable for transplant as contemplated by the present invention, requires assaying the immunotype ('tissue typing') of the recipient and then selecting immunocompatible stem cell populations. There are two techniques used currently for tissue typing, serological (the lymphocytotoxicity test), and molecular (DNA based) techniques. These may be used to select stem cell populations as well, and are described below.

1. Serological Techniques

For serological typing of the recipient, in the present invention, two samples of approximately 20 ml of anti-coagulated blood are required from the recipient for a full class I and class II tissue type. For class I typing, one sample of blood is treated with sodium citrate, and then defibrinated so as to remove platelets as they may result in false negative reactions. The sample is then layered onto a density gradient medium and centrifuged so as to separate red blood cell and polymorphs from lymphocytes. The red cell and polymorphs sediment, and a band of lymphocytes is removed to another tube and washed. The lymphocytes are then counted and adjusted to a standardized cell count, such as 1.5–2.0 million cells per ml, for a lymphocytotoxicity test. The counted cells and typing sera are incubated in wells of a test plate, such that the HLA anti-sera bind to specific cell membrane target antigens on the surface of the lymphocytes. See FIG. 4A for serological specificities of class I alleles. Rabbit serum, or complement, is then added to lyse the cells. The cells will lyse, only when there is an antibody-antigen complex formed on the cell membranes of the lymphocytes, which then activates complement leading to cell lysis. Lysed cells are detected by the entry of a stain into the dead cells- a positive reaction. If there is no lysis, cells do not stain indicating a negative reaction.

For class II typing, the second sample of blood is treated with EDTA. The sample is then incubated with immunomagnetic beads, (superparamagnetic monodisperse polymer particles coated with monoclonal antibodies) and placed in a magnetic field. As class II antigens are expressed on B cells, the immunomagnetic beads are coated with a monoclonal antibody with a specificity for B cells. The B cells and the beads are captured by the magnetic field, washed, and counted using standard techniques. A standard volume, such as 60 μl, is then used for a lymphocytotoxicity test as described above. See FIG. 4B for serological specifications of class II alleles. The lyphocytotoxicity assay is further described by Hui et al, *Handbook of HLA Typing Techniques*, p. 194 (1993).

The lymphocytotoxicity test may be used to type stem cells as well. A panel of immunologically well-characterized anti-sera are added to a sample of stem cells, from a related or unrelated donor, and incubated. Rabbit serum, a source of complement, is then added to the mixture, which is activated if the anti-sera bind the HLA antigens on the stem cell surfaces. Upon activation, complement will lyse the cells allowing them to absorb a standard stain, and be detected.

Because it is unclear whether HS cells might not have carried the proper HLA molecules, at this early stage of development, molecular testing (see section 2 infra) should also be used.

In an alternative embodiment, a mixed leukocyte culture test (MLC) may also be used for recipient and stem cell class II molecules. This test, described in Bach et al. (1964), *Lymphocyte Interaction: A Potential Histocompatibility Test In Vitro, Science* 143:813–814, measures the response of a potential recipient's T-cells to alloantigens present on the cells of a potential donor, and is incorporated by reference herein.

2. Molecular Techniques

Genomic DNA from a blood sample of the recipient, or stem cells is required for these techniques. Genomic DNA is first amplified using a polymerase chain reaction (PCR) procedure known to one skilled in the art. The PCR amplified blood DNA can then be typed using two techniques, digestion with restriction enzymes (Restriction Fragment Length Polymorphism analysis), or hybridization with multiple sequence specific oligonucleotide probes (SSOP). The RFLP analysis is preferred as a reliable and more convenient method as it does not require radioactive labeling. It incorporates enzymes that recognize specific sites in some alleles, therefore a specific HLA-haplotype may be detected by simply checking whether the enzyme digests the amplified DNAs. FIG. 5 lists restriction endonucleases that may be used for class II typing. Detailed methodology may be obtained from Hui et al, *Handbook*, at 9.

The SSOP analysis requires the amplified DNA to be immobilized on a nylon membrane, and then hybridized with selected radioactive oligonucleotide probes directed to specific HLA-alleles. FIG. 6 shows a list of SSOPs that may be used for class II typing. A modification of this technique, the sequence specific primer typing, (SSP), may also be used. Here, the specificity of the typing system is part of the PCR reaction. Oligonucleotide primers are used to amplify specific HLA-alleles, hence completely matched primers will be more efficiently used in the PCR reaction and may then be detected using agarose gel electrophoresis and transillumination.

Other PCR methods such as class II matching by PCR fingerprinting, Hui et al, *Handbook*, at 99, PCR characterization of polymorphic microsatellite loci of HLA, Martin et al., Immunogenetics 47:131–138, (1998), are also contemplated by the present invention.

Characterization of polymorphic microsatellite loci of HLA is a preferred technique that predicts the HLA haplotype of a recipient and a donor, and is especially useful when the donor and recipient are related. As described by Martin et al., supra, large numbers of microsatellite repeats are found interspersed in the human genome. These microsatellites are highly polymorphic and are inherited in a Mendelian fashion, thus giving them utility as genetic markers. Twelve microsatellites within or near the HLA were typed and sequenced by Martin et al. See FIG. 7 for PCR primers used to sequence microsatellites. Further, alleles were designated according to size. Linkage disequilibrium between these microsatellites and certain HLA alleles suggests that these microsatellites may predict HLA typing, and may be used as markers. FIG. 8 shows a map of the HLA-I, II and III regions and the relative position of 12 microsatellites.

D. Method for Selecting Genotype

In certain instances, it is necessary to select for the presence of a target genotype. As noted above, the "target" genotype in the context of the present invention will be that genotype that is the non-mutant or "normal" form, i.e., the genetic sequence that is not linked to pathology. Thus, in those instances wherein the germ cell donor is affected with or is a carrier for a genetically linked disease or disorder, it is necessary to assay the genotype of each HS cell system arising from each donor homozygous post-meiosis I diploid germ cell and select only those populations carrying the desired target genotype. Those populations carrying the mutant genotype should be eliminated from further development. Recall, each donor germ cells is diploid and homozygous for a particular haplotype. Thus, each population of cells arising therefrom (i.e., the mitotic activation of post-meoisis I diploid germ cell system and the stemplasm system) will homogeneously carry one haplotype or the other, not both.

There are numerous techniques for assaying the genetic constitution or "genotype" of a cell population. Most begin with the extraction of a sample of genetic material (e.g. genomic DNA or mRNA) from which cDNA may be derived, from a representative cell. The sample is typically amplified, using techniques such as PCR, and cloned to derive a partial or complete genetic "library". The library can then be screened for the presence of the normal or mutant sequence. As noted previously, those populations containing the normal sequence are selected for further development; those containing the mutant sequence (i.e., that which is associated with pathology) will be eliminated. The genetic mutation may be detected by a number of methods utilizing techniques including, but not limited to, gel-based sequencing, non gel-base sequencing, and genetic markers. The resulting sequence can be automatically scanned for the presence of the mutant or target (i.e., normal) sequence.

1. Gel-Based Sequencing

The most common nucleic acid sequencing method involves the separation of the DNA fragments, typically from genomic DNA or cDNA cut by specific cleavages or synthesized by DNA polymerases, using a gel, such as a polyacrylamide gel. Examples of gel-based sequencing techniques include, but are not limited to, Maxam-Gilbert sequencing (also called the chemical degradation method) and Sanger sequencing (also called the chain termination or dideoxy method).

Maxam-Gilbert sequencing (Maxam et. al., Proc. Natl. Acad. Sci. USA 74:560–564, 1977, incorporated by reference herein) uses chemicals to cleave DNA at specific bases, resulting in fragments of different lengths. A refinement to the Maxam-Gilbert method known as multiplex sequencing enables investigators to analyze about 40 clones on a single DNA sequencing gel.

Sanger sequencing (Sanger et. al., Proc. Natl. Acad. Sci. USA 74 5463–5467, 1977, incorporated by reference herein) involves using an enzymatic procedure to synthesize DNA chains of varying length in four different reactions, stopping the DNA replication at positions occupied by one of the four bases, and then determining the resulting fragment lengths.

Maxam-Gilbert and Sanger, differ primarily in the way the nested DNA fragments are produced. Both methods work because gel electrophoresis produces very high resolution separations of DNA molecules; even fragments that differ in size by only a single nucleotide can be resolved. Almost all steps in these sequencing methods are now automated. Certain known disease genes can be sequenced with technologies as high voltage capillary and ultrathin electrophoresis to increase fragment separation rate and use of resonance ionization spectroscopy to detect stable isotope labels.

2. Non Gel-Based Sequencing

Non gel-based sequencing technologies, which aim to increase efficiency by several orders of magnitude, can also be used. These technologies include but are not limited to (a) enhanced fluorescence detection of individual labeled bases in flow cytometry; (b) direct reading of the base sequence on a DNA strand with the use of scanning tunneling or atomic force microscopies; (c) enhanced mass spectrometric analysis of DNA sequence, and (d) sequencing by hybridization to short panels of nucleotides of known sequence.

Sequencing by hybridization (SBH) can be applied to the efficient identification and sequencing one or more DNA samples in a short period of time. The procedure has many applications in DNA diagnostics, forensics, and gene mapping. It also may be used to identify mutations responsible for genetic disorders and other traits, to assess biodiversity and to produce many other types of data dependent on DNA sequence.

There are several approaches for sequencing by hybridization (SBH). In SBH Format 1, DNA samples are arrayed and labeled probes are hybridized with the samples. Replica membranes with the same sets of sample DNAs may be used for parallel scoring of several probes and/or probes may be multiplexed. Techniques for arraying and hybridization of DNA samples on the nylon membranes are well developed. Each array may be reused many times. Format 1 is especially efficient for batch processing large numbers of samples.

In SBH Format 2, probes are arrayed and a labeled DNA sample fragment is hybridized to the arrayed probes. In this case, the complete sequence of one fragment may be determined from simultaneous hybridization reactions with the arrayed probes. For sequencing other DNA fragments, the same oligonucleotide array may be reused. In a variant of Format 2, DNA anchors are arrayed and ligation is used to determine oligosequences present at the end of the target DNA.

In Format 3, two sets of probes are used. One set may be in the form of arrays and another, labeled set is stored in multiwell plates. In this case, target DNA need not be labeled. Target DNA and one labeled probe are added to the arrayed set of probes. If one attached probe and one labeled probe both hybridize contiguously on the target DNA, they are covalently ligated, producing a sequence twice as long to be scored. The process allows for sequencing long DNA fragments, e.g. a complete bacterial genome, without DNA subcloning in smaller pieces.

For additional details on SBH, see U.S. Pat. Nos. 5,503,980, 5,683,881, and 6,025,136, incorporated by reference herein. See also Bainst, W., et al., J. Theoret. Biol., 135: 303–307 1988; Matthews, J. A., et al., Anal. Biochem., 169, 1–25, 1988; Syvanen, A. C., Medical Biology, 64, 313–324 1986; and Lehrach, H., et al., Genome Analysis, 1, 39–71, 1990, the contents of which are all incorporated by reference herein.

3. Genetic Markers

Genetic markers, short sequences that correlate to the presence of a particular gene sequence, can be used to detect the presence of a mutant or normal gene. Examples of genetic markers useful in the context of the present invention include, but are not limited to, sequence tagged sites (STSs), short sequences that are standard markers for physical mapping, and expressed sequence tags (ESTs), unique markers for identifying expressed genes. These markers provide a means of rapidly identifying most human genes. Other applications of the EST approach include determining locations of genes along chromosomes and identifying coding regions in genomic sequences.

Genetic markers have the greatest utility when they are highly heritable, multiallelic, and numerous. Most genetic markers are highly heritable because their alleles are determined by the nucleotide sequence of DNA, which is highly conserved from one generation to the next, and the detection of their alleles is unaffected by the natural environment. Markers have multiple alleles because, in the evolutionary process, rare, genetically-stable mutations in DNA sequences defining marker loci arose and were disseminated through the generations along with other existing alleles. The highly conserved nature of DNA combined with the rare occurrence of stable mutations allows genetic markers to be both predictable and discerning of different genotypes.

DNA fingerprinting is a broad term used to designate methods for assessing sequence differences in DNA isolated from various sources, e.g., by comparing the presence of marker DNA in samples of isolated DNA. Typically, DNA fingerprinting is used to analyze and compare DNA from different species of organisms or DNA from different individuals of the same species. DNA sequence differences detected by fingerprinting are referred to as DNA polymorphisms. The presence of a DNA polymorphism in an organism's DNA can serve to indicate that the genetic origin of such an organism is different from the genetic origin of organisms whose DNA does not have the polymorphism. Such polymorphisms can result, e.g., from insertion, deletion, and/or mutation events in the genome.

Many genetic-marker technologies are adaptable to fingerprinting, including restriction-fragment-length polymorphism (RFLP) (Bostein et al., Am. J. Hum. Genet. 32:314–331, 1980); single strand conformation polymorphism (SSCP) (Fischer et al., Proc. Natl. Acad. Sci. USA 80:1579–1583,1983; Orita et al., Genomics 5:874–879 1989); amplified fragment-length polymorphism (AFLP) (Vos et al., Nucleic Acids Res. 23:4407–4414, 1995); microsatellite or single-sequence repeat (SSR) (Weber, J. L. et al., Am. J. Hum. Genet. 44:388–396 1989); rapid-amplified polymorphic DNA (RAPD) (Williams et al., Nucleic Acids Res. 18:6531–6535 1990); sequence tagged site (STS) (Olson et al., Science 245:1434–1435, 1989); genetic-bit analysis (GBA) (Nikiforov et al., Nucleic Acids Res. 22:4167–4175, 1994); allele-specific polymerase chain reaction (ASPCR) (Gibbs et al., Nucleic Acids Res. 17:2437–2448, 1989;, Newton et al., Nucleic Acids Res. 17:2503–2516, 1989); nick-translation PCR (e.g., Taq-Man.TM.) (Lee et al., Nucleic Acids Res. 21:3761–3766, 1993); and allele-specific hybridization (ASH) (Wallace et al., Nucleic Acids Res. 6:3543–3557, 1979); Sheldon et al., Clin. Chem. 39(4):718–719 1993). Each of the above-noted articles are incorporated by reference herein.

Kits for RAPD and AFLP analyses are commercially available, e.g., from Perkin Elmer Applied Biosystems (Foster City, Calif.). For example, the restriction fragment length polymorphism (RFLP) technique employs restriction enzyme digestion of DNA, followed by size separation of the digested DNA by gel electrophoresis, and hybridization of the size-separated DNA with a specific polynucleotide fragment. Differences in the size of the restriction fragments to which the polynucleotide probe binds reflect sequence differences in DNA samples, or DNA polymorphisms. See Tanksley, *Biotechnology* 7:257–264 (1988), incorporated by reference herein.

PCR-based fingerprinting methods result in the generation of a large number of reproducible DNA fragments of specific size that can be separated, typically by gel electrophoresis. These fragments are visualized to produce a "fingerprint" of the amplified DNA. Visualization of the size-separated fragments is effected either by direct visualization, e.g., with a fluorescent dye, by hybridization with a polynucleotide probe, or by labeling the amplification products during PCR (radioactively or fluorescently), followed by detection of the labeled products in the gel. These fingerprints have a variety of uses: parentage analysis; linkage analysis of specific traits; analysis of the degree of generic relationship between individuals within a species; and analysis of phylogenetic relationships between species. This has considerable commercial use in agriculture for marker assisted selection of genetic traits specific to particular genotypes (e.g., in crops or animals), identification and mapping of quantitative trait loci (QTLs) and the like.

For additional details on genetic markers and techniques for detecting genes without sequencing, see U.S. Pat Nos. 6,141,657, 5,683,880, and 6,100,030, all incorporated by reference herein.

E. Methods for Directed Differentiation of HS Cells

HS cells can be induced to differentiate into various types of tissues originating from all three germ layers (endoderm, mesoderm, and ectoderm) including, but not limited to, skin, hair, nervous tissue, pancreatic islet cells, bone, bone marrow, pituitary gland, liver, bladder, and other tissues having diagnostic or therapeutic utility in animals, including humans as described in U.S. patent application No.: 09/997,240 and U.S. Provisional Application Ser. No. 60/253,943, fully incorporated by reference herein.

One skilled in the art of differentiation techniques, particularly those developed for differentiation of ES cells and embryonic carcinoma (teratocarcinoma) cells, can induce a pluripotent HS cell to differentiate into a desired type/of tissue without undue experimentation.

The pluripotent isolated HS cells of the present invention can be differentiated into selected tissues for a variety of therapeutic uses including the in vitro culture of differentiated tissues for purposes of study, diagnostics, or for implantation into an individual. Preferably, HS cells will be used therapeutically in the individual that provided the donor material for HS formation. In females, this may be achieved by activation of post-meiosis I diploid oocytes, or by fusion two haploid oocytes; in males, this may be achieved by activation of secondary spermatocytes or fusion of spermatids, or by transferring sperm nuclei to enucleated oocytes.

Well known methods used for isolating and culturing ES cells can be adapted for use with HS cells. Exemplary procedures are provided by Hogan et al., supra, pp. 254–262, 265–272. For example, Hogan et al. describe the optimal culture media as a 7.2–7.4 pH buffered bicarbonate media, such as Dulbecco's modified Eagle's medium, containing glucose and sodium pyruvate, further supplemented with glutamine (2 mM), nonessential amino acids (0.1 mM), mercaptoethanol (0.1 mM) or monothioglycerol (0.15 mM), gentamycin (50 μg/ml), 15% serum (e.g. fetal bovine serum), and leukemia inhibitory factor (LIF). A mixture of trypsin and EDTA in $Ca^{++}/Mg^{++}$-free phosphate buffered saline can be used to detach cells from tissue culture dishes and dissociate them from one another. Stem cells are preferably cultured on a feeder cell layer in medium supplemented with LIF to provide factors that enhance the proliferation and maintain the undifferentiated state of stem cells. Fibroblasts, particularly mouse embryo fibroblasts (MEF) and STO mouse fibroblasts, are the preferred feeder cells. Feeder cells should be mitotically inactivated, by treatment with mitomycin C, or gamma radiation. Additional types of feeder cells may used or a feeder-free system may also be used. Detailed protocols for each step in the preparation and maintenance of viable stem cell cultures are provided by Hogan et al., supra.

Similarly, methods for isolating individual colonies of ES cells and expanding them to a sufficient number to allow isolation and screening of DNA can be applied to HS cells. For example, Hogan et al., supra, at pp. 279–281, describe stem cell isolation techniques including: the extraction and transfer of a trypsinized colony to single wells of a culture dish using an automatic pipettor and extraction and transfer of a non-trypsizinized colony to a microdrop of trypsin/EDTA using a sterile, glass Pasteur pipette attached to a tubing and a mouthpiece. Preferred clones can be identified and assayed using rapid techniques and PCR.

To minimize the danger of accumulating chromosomal anomalies, vials of stock should be frozen and stored as soon as possible. Methods for proper freezing and storage of cultures are well known for ES cells, and may be applied to HS cells. See, for example, Hogan, et al., supra, pp. 283, setting forth a detailed protocol for freezing, trypsinizing, pelleting and resuspending samples from cell cultures. Methods for differentiation of pluripotent cells are discussed below. These methods are designed to be an illustrative not an exhaustive, list of methods for differentiating pluripotent cells including the HS cells of the present invention. The present invention can be practiced using differentiation methods known in the art, including techniques not recited here, or not yet discovered.

For example, Hole (Cells Tissues Organs 165:181–189, 1999, and incorporated by reference herein) describes methods for directing the differentiation of hematopoietic cells from embryonic stem cells in vitro that may be adapted to differentiate HS cells. Furthermore, Doetschman et al., Embryol. Exp. Morphol. 87:27–45, 1985, incorporated by reference herein, suggests that the withdrawal of leukemia inhibitory factor (LIF) from ES cells grown in suspended culture results in the formation of cystic embryoid bodies containing blood islands made up of erythrocytes and macrophages. The production of other hematopoietic cells, including neutrophils, mast cells, macrophages and erythroid cells, from stem cells has also been described (See, e.g., Wiles and Keller, Devel. 111:259–267,1991; Keller et al, Mol. Cell. Biol. 13:473–486, 1993a; and Lieschke and Dunn, Exp. Hematol. 23:328–334, 1995; each of which are hereby incorporated by reference herein in their entirety). These methods may be adapted for use with HS cells of the present invention without undue experimentation.

The techniques described by Cho et al., Proc. Natl. Acad. Sci. USA 96:9797–9802, 1999, incorporated by reference herein, for efficiently differentiating ES cells into mature Ig-secreting B lymphocytes can also be adapted for use with the HS cells of the present invention. Likewise, Dani, Cells Tissues Organs 165: 173–180, 1999 incorporated by reference herein, describes a method for differentiating ES cells into adipocytes. For example, the treatment of embryoid bodies at an early stage of their differentiation with retinoic acid (RA) for a short period of time appears to be linked to adipogenesis.

Techniques for eliciting the differentiation of stem cells into a variety of neuronal cells and neurons are described by Okabe et al., Mech. Dev. 59: 89–102, 1996, incorporated by reference herein. Likewise, stem cell-derived oligodendrocytes and neurons having particular use in treating injured spinal cords are described by McDonald et al., Nature Medicine 5:1410–1412, 1999 incorporated by reference herein. These techniques can be adapted for use with HS cells of the present invention without undue experimentation.

The use of accessory cell lines, such as OP9, to derive particular cell lineages is also contemplated. See, for example, Nakano el al., Science 265:1098–1101, 1994, (incorporated by reference herein) and Nakayama el al., Blood 91:2283–2295, 1998 (incorporated by reference herein) that relate to erythroid, myeloid and lymphoid lineages.

Techniques for eliciting the differentiation of HS cells of the invention into follicular cells, as well as epidermal cells are also contemplated. See, for example, Taylor et al., Cell 102: 451–361, 2000 (incorporated by reference herein). The expression of particular regulatory genes may also be used to direct differentiation. See, for example, Hole et al., Blood 90:1266–1276 1996a, and Battieres Clin. Hematol. 3:467–483, 1997 (incorporated by reference herein), relating to hematopoietic genes. Likewise, nuclear regulatory factors involved in lipid metabolism, including but not limited to PPARs (PPAR$\delta$ and PPAR$\gamma$) and C/EBP$\delta$ (C/EBP$\beta$, C/EBP$\delta$ and C/EBP$\alpha$), may also be triggers of terminal differentiation of preadipocytes into adipocytes. Such factors would find utility in the context of the differentiation methods of the present invention.

Depending on the function needed, differentiation may be assessed by detecting expression of a gene specific for differentiation, by detecting tissue-specific antigens, by examining cell or tissue morphology, by detecting functional expression such as ion channel function; or by any means suitable for detecting the differentiation of HS cells.

Methods for inducing differentiation of embryonal carcinoma (EC) cells into a variety of embryonic and extraembryonic cell types can be used to induce differentiation of HS cells (Andrews, APMIS 106:158–168 1998). HS cells can undergo directed differentiation in vitro by exposure to various factors known to trigger cell commitment and differentiation into a desired cell type or tissue. Many in vitro differentiation schemes involve the removal of growth factors known to favor initiation of differentiation. Once these factors are removed from the medium, the stem cells, growing in suspension without feeder cells, form clusters, known as embryoid bodies, within which descendants of all three embryonic germ layers can be found. The presence of certain cell lineages within the embryoid body can be enhanced through supplementation of the medium with additional growth factors and chemicals. The resulting cell population will then contain an increased proportion of a desired cell type, which then can be selectively isolated. See Edwards et al., Modern Trend., 74(1): 1–7, 2000 (incorporated by reference herein) for a discussion of pluripotent stem cells and their use in medicine.

Illustrative examples of such differentiation control factors include but are not limited to cytokines, hormones, and cell-regulating factors such as LIF, GM-CSF, SCF, IL-3, thyroid hormone (T3), stem cell factor (SCF), fibroblast growth factor (FGF-2), -platelet derived growth factor (PDGF), ciliary neurotrophic factor. While stimulating cytokines such as GM-CSF, SCF, and IL-3 have been shown to promote differentiation (see Keil F, et al., Ann. Hematol.

79(5):243–8, 2000 (incorporated by reference herein)), inhibitory factors such as LIF has been shown to maintain mouse embryonic stem (ES) cells in the undifferentiated pluripotent state (Zandstra PW, et al., Blood 96(4):1215–22, 2000 incorporated by reference herein). While SCF has been shown to stimulate the differentiation of chicken osteoclasts from their putative progenitors (van't Hof R J, et al., FASEB J. 1997 March; 11(4):287–93, 1997 incorporated by reference herein), FGF-2 has been shown to play a role both in initiating lactotrope differentiation and maintaining Prolactin expression in immortalized GHFT cells, thereby suggesting a mechanism for controlling differentiation of stem cells into different anterior pituitary cells (Lopez-Fernandez J, et al., J. Biol. Chem. 275(28):21653–60, 2000 incorporated by reference herein). Platelet-derived growth factor (PDGF-AA, -AB, and -BB) supports neuronal differentiation while ciliary neurotrophic factor and thyroid hormone T3 generate clones of astrocytes and oligodendrocytes (Johe KK, et al., Genes Dev. 10(24):3129–40, 1996 incorporated by reference herein).

HS cells can be induced to differentiate by transplantation in vivo, preferably in situ, where the cells undergo histologic and functional differentiation and form appropriate connections with host cells. Endogenous regulation factors located in the transplant site can direct the differentiation of the stem cell into a particular type of differentiated cell or tissue. Alternatively, groups of divergent differentiated cells and/or tissues result from stem cells transplanted to the hypodermis, the peritoneum, and the renal capsule. See Hogan, supra, pp. 183 to 184, for a detailed description of the kidney capsule implantation procedure.

Differentiation of pluripotent HS cells into various endodermal cell types has great therapeutic implications, including use for transplantation purposes, or to enhance the HS cells can be uptake and processing of nutrients, or to direct pattern formation, induced to differentiate into endodermal progenitor cells by treatment with high doses of RA or by members of the transforming growth factor β superfamily including bone morphogenetic protein (BMP)-2 (Pera and Herzfeld, Reprod. Fert. Dev. 80:551–555 1998). Some HS cell lines can also be induced to differentiate in distinct culture systems. For example, non-neural differentiation can be induced by hexamethylene bisacetamide (HMBA) (Andrews, APMIS 106:158–168 1998). BMP-2 can be used to specifically trigger differentiation into parietal, or visceral endoderm (Rogers et at., Mol. Bio. Cell. 3:189–196 1992). BMPs are molecules that can induce cartilage and bone growth in vivo, but BMP messages are also expressed in many non-bony tissues, including developing heart, hair follicles and central nervous system, indicating a pivotal role in cell commitment and differentiation.

F. Prophylactic and Therapeutic Utilities

One embodiment of the present invention is a method of growing cells and tissues that may be transplanted into an affected person for the treatment of diseases including but not limited to hereditary, or genetic diseases, neurological or neurodegenerative diseases, traumatic injuries and cancers. Another cosmetic application of the present invention is skin grafts for hair replacement and/or other such applications.

HS cells can be induced to differentiate into various types of tissues originating from all three germ layers (endoderm, mesoderm, and ectoderm) including but not limited to skin, hair, nervous tissue, pancreatic islet cells, bone, bone marrow, pituitary gland, liver, bladder, and other tissues having diagnostic or therapeutic utility in animals, including humans as described in U.S. patent application Ser. No. 09/997,240, and U.S. Provisional Application Ser. No. 60/253,943.

The present invention provides a method of treating a disorder or disease state by generating, in situ or in vitro, suitable replacement cells, groups of cells, tissues or organs from isolated HS cells with pre-selected immunotype and/or genotype. Methods of directing differentiation of cells in situ or in vitro are described in the preceding section, and in U.S. patent application Ser. No. 09/997,240, and U.S. Provisional Application Ser. No. 60/253,943.

Illustrative disorders and disease states include but are not limited to traumatic injury (e.g., post-trauma repair and reconstruction, for limb replacement, spinal cord injury, burns, and the like) and birth defects; pathological and malignant conditions of the cells, tissues, and organs (e.g., cancer); and degenerative and congenital diseases of the cells and tissues of the muscles (e.g., cystic fibrosis, muscular dystrophy, cardiac conditions), nerves (e.g., Alzheimer's, Parkinson's, and multiple sclerosis), epithelium (e.g., blindness and myopathy, atherosclerosis and other stenotic vascular conditions, enzyme deficiencies such as Crohn's disease, and hormone deficiencies such as diabetes), and connective tissues (e.g., immune conditions and anemia). HS-derived cells and tissues may be grafted or transplanted to a subject in need, preferably using the subject's own donor material.

Currently, gene therapy for the treatment of hereditary diseases has not had much success. There are many reasons for this, the most significant being the inability to place normal DNA into a patient's cells such that it is stably integrated and expressed. Additionally, gene-replacement therapy may be too targeted, for example, gene-corrected T-cell therapy, where T-cells with normal DNA have been transplanted into patients to treat severe combined immunodeficiency disease (SCID), including the ADA deficiency type. The problem faced here is that the corrected T-cells are primed for only one type of antigen, and a whole range of immune response cannot be derived from them. Yet another problem faced by current application of gene therapy, is that the product or the exact function of the mutant gene may not be known or the genetic disease may involve an entire cascade of factors untreatable by gene-replacement.

The present invention provides a means to bypass these concerns. HS cells, for example in the context of SCID may be transplanted into the bone marrow of the patient such that local endogenous factors derive an entire range of T- and B-cells. Issues of HLA compatibility, or graft vs. host disease would not be an issue here as the cells would be immunologically compatible. Similarly, HS cells may be useful for the treatment of genetic diseases that are caused by mutations that result in a missing gene product or the absence of an enzyme. For example, currently the treatment of Phenylketonuria is elimination of phenylalanine from the diet of the patient, as the patient does not produce the enzyme required to convert it to tyrosine. Differentiated HS cells may be transplanted into these patients to produce the required enzyme. Similarly, HS cells may find transplant applications in diseases like Haemophilia A, where differentiated HS cells may produce a missing gene product, namely Clotting Factor VIII.

Another embodiment of the invention is a method of inducing HS cells to differentiate by transplantation in vivo, preferably in situ, thereby generating a stemplasm, wherein the cells undergo histologic and functional differentiation and form appropriate connections with host cells. Endogenous regulation factors located in the transplant site can direct the differentiation of the stem cell into a particular type of differentiated cell or tissue. Alternatively, groups of divergent differentiated cells and/or tissues result from stem cells transplanted to the hypodermis, the peritoneum, and the renal capsule. These and other methods are described in U.S. patent application Ser. No. 09/997,240, and U.S. Provisional Application Ser. No. 60/253,943.

The pluripotent isolated HS cells of the present invention can also be differentiated into selected tissues by in vivo differentiation in immuno-compromised animal followed by isolation of the said tissues for a variety of therapeutic uses. And the HS cells can also be cultured and differentiated in vitro for purposes of study, or diagnostics.

G. Depository of HLA typed HS cells

HS cells are homozygous and carry only one HLA haplotype. Thus, a donor HS cell has only one HLA haplotype to be matched with the recipient instead of two, as in heterozygous stem cells. As discussed above, there are 22 different HLA A antigens, 42 different B antigens, 9 different Cw antigens and 18 DR antigens. With such a large number of polymorphic HLA haplotypes, a complete match of two haplotypes between a recipient and a donor is quite difficult. In a best case scenario, such as when there is linkage disequilibrium and the presence of specific ethnic HLA haplotypes, the chance of finding a two haplotype match ranges from one in 1,000 to one in several million. However, in the same scenario, a one haplotype match could be achieved in less than 1 in 200 persons for the common haplotypes (see Martin et al., supra., showing total disequilibrium of common haplotype of around 172 for the Caucasian population in the United States). Thus, HS cells can be taken from random donors of multiple ethnicities to provide a depository or bank of HS cell populations that immunohistologically match at least one haplotype carried by individuals in the population at large. The depository needs only contain about 200 different HS cell lines, each having a distinct HLA haplotype, to service most of the general population (i.e., provide immunohistocompatible cells suitable for transplant).

In a preferred embodiment, the depository contents are catalogued, for example as a searchable computer database, to facilitate remote, rapid screening by practitioners around the world. The present invention provides a method for producing a population of genotyped homozygous stem (HS) cells from multiple donor. Ideally, the donors will be selected for having a high probability of having widely divergent HLA haplotypes. The donors will then be assayed for the HLA haplotype and genotype. Then HS are derived from said donors by mitotically activating donor homozygous post-meiosis I diploid germ cells to develop multiple blastocyst-like masses, each of which contains an inner cell mass (ICM) that is homozygous for a particular allele, isolating HS cells from the selected ICM, and culturing said HS cells to create each of the HS cell lines, assaying the genotype of each said HS cell line, and cataloging each HLA haplotype and genotype associated with each HS cell line generated.

The following examples further illustrate experiments which have demonstrated reduction to practice and utility of selected preferred embodiments of the present invention, although they are in no way a limitation of the teaching or disclosure of the present invention as set forth herein.

H. EXAMPLES

Example 1

Homozygous Stem Cell Formation, and their Differentiation into Progenitor Cells and Various Tissues of the Three Embryonic Germ Layers within Stemplasms

Example 1(a)

Derivation of HS Cells from Mouse Post-Meiosis I Oocytes by Activation Followed by Prevention of the Extrusion of the Secondary Polar Body Three eight-week old female C57/BDA2 F1 mice (Charles River Laboratories, Wilmington, Mass.), were superovulated by sub-peritoneal injections of 5 IU/100 ul of pregnant mare's serum gonadotropin (PMS; PCCA, Houston, Tex. (29-1000-1BX)), and 5 IU/100 µl of human chorionic gonadotropin (HCG; Sigma, St. Louis, Mo., (C8554)) with 48 hours apart between the injections. Seventy-three oocytes were harvested about 17 hours after the HCG injection, and the cumulus was removed by incubating the freshly obtained oocytes in a drop (~300µl) of hyaluronidase (Sigma, H4272) diluted in M2 media (M7167, Sigma) at final concentration of 0.3 mg/ml, followed by 3 washes with HEPES buffered M2 media before further handling. Oocytes were then activated by treatment with 5 µM calcium ionophore (Sigma,C7522) solution at room temperature for five minutes followed by 2 washes with HEPES buffered M2 media. The oocytes were further subjected to incubation in 5 mM 6-dimethylaminopurine (6-DMAP) (Sigma, D2629) in M16 bicarbonate-buffered culture media (Sigma, M7292) at 5% $CO_2$ and 37° C. for 3 hours. After the incubation, oocytes were washed three times with M16 media and incubated in a drop of M16 media under mineral oil until blastocyst-like masses developed (4 to 5 days). The blastocyst-like masses then naturally hatch out of the surrounding zona shell, and the blastocyst-like masses were then transferred to a mitomycin-C treated murine embryonic feeder cell layer and cultured for at least 15 days in ES medium (DMEM (Gibco, Life Technologies, Rockville, Md., 11995–065) with 20% fetal bovine serum (Gibco, 16141-079) and 1,400 U/ml of LIF (Chemicon, ESG1106) for stem cell line formation.

Alternatively, immunosurgery was performed to remove trophoblast cells from blastocyst-like masses before culturing on the feeder by the following procedure. Hatched blastocyst-like masses were first incubated with anti-mouse Thy-1 rabbit serum (1:10 dilution in stem cell medium, Accurate Chemical, Westbury, N.Y., ACL2001) and anti-human lymphocytes rabbit serum (1:10 dilution in stem cell medium, Accurate Chemical, CL8010) for one hour at 37° C. After washes three times with M2 medium the blastocyst-like masses were then incubated with guinea pig complement (1:10 dilution in stem cell medium, Accurate Chemical, ACL4051) for 30 minutes at 37° C. The complement-treated cell masses were then washed 3 times in the M2 medium and transferred to a mitomycin-C treated murine embryonic feeder cell layer for further culturing in stem cell medium consisted of 80% Dulbecco's modified Eagle's medium (no pyruvate, high glucose formulation; Gibco-BRL) supplemented with 20% fetal bovine serum (Gibco-BRL), 1 mM glutamine, 0.1 mM -mercaptoethanol (Sigma), 1% nonessential amino acid stock (Gibco-BRL) and 1,400 U/ml LIF (Chemicon, ESG1106).

After 15 days, inner cell mass-derived outgrowths formed and were dissociated into clumps by mechanical dissociation with a micropipette and replated on murine fibroblasts feeder in fresh stem cell medium. Individual colonies with a uniform undifferentiated morphology were individually selected by micropipette, mechanically dissociated into clumps, and replated. Once established and expanded, cultures were passaged by 5 minutes exposure to Trypsin/EDTA solution (0.05%/0.5%, Gibco-BRL) followed by further culturing on feeder cells and fresh stem cell medium.

Murine embryonic fibroblasts feeder cells were purchased from Stemcell, Inc. (00308), and passaged 2–3 times before use. To mitotically inhibit the feeder cells, one 60-mm dish of confluent-expanded feeder cells was treated with 5 ml of 10 µg/ml mitomycin-C (Sigma, M4287) in DMEM/10% FBS medium at 37° C. for three hours. Treated feeder cells were then washed with 5 ml DMEM/10% FBS three times, and collected by trypsinization at 37° C. for 5 minutes, followed by neutralization with 5 ml DMEM/10% FBS medium and centrifugation at 1000 rpm for 5 minutes. The mitomycin-treated cell pellet obtained was then resuspended in 15 ml DMEM/10% FBS medium, plated on three 60-mm dishes (5 ml of cell suspension/dish), and incubated at 37° C. overnight before use.

Example 1(b)

Derivation of HS Cells Homozygous for a Specific Genotype and an Immunotype From Female C57/DBA2 Hybrid Mice Five female C57DBA2 hybrid mice heterozygous for most genetic loci and H-2 (mouse MHC) were superovulated as described in example 1(a) for HS cells population. Eleven cell lines were derived and were propagated in culture and then cryopreserved. Cells from each line at around passage 5 were immunotyped for I-E-beta in H-2 loci (sequences of PCR primers are: Eb1: CAG AAC CTG AGT CCT GGG CG; Eb2: AGC AGA CCA GGA GGT TGT GG) and genotyped for D2mit42 using microsatellite markers (Research Genetics).

Methods for genomic DNA extraction, PCR amplification, and genetic analysis (using D2mit42 microsatellite marker) of mouse HS cells were as describe in example 1(f). Immunotyping of H-2 (I-E-beta) was performed by separating the PCR products of the H-2 alleles using single-strand conformational polymorphism (SSCP) analysis on a MDE gel (FMC Bioproducts). Results of genotyping and immunotyping of two representative HS cell lines derived from C57/DBA2 hybrid mice are shown in FIGS. 9A–F, in which a C57/DBA2 mouse (FIG. 9A), and her superovulated oocytes-derived blastocyst-like masses (FIG. 9B) and two representative colony (FIGS. 9C and 9D) from two different HS cell lines are shown. The genotype (FIG. 9E) and immunotype (FIG. 9F) of the donor mouse (Lane 1), HS cell line-1 (Lane 2), and HS-cell line-2 (Lane 3) are also demonstrated.

Example 1(c)

Development of Blastocyst-Like Cell Masses from Human Diploid Oocytes by Activation Followed by the Prevention of the Extrusion of the Secondary Polar Body.

Female ovum donors underwent down-regulation with leurpolide acetate (Lupron: TAP Pharmaceuticals, Deerfield, Ill.) and then began COH (Controlled Ovarian hyper-stimulation) by receiving follicle stimulating hormone (FSH) (Serono, Gona-F) treatment at a dosage of 300 IU/day to induce an appropriate multifollicular response. When ultra-sonographic criteria for follicular maturity were met, a single 10,000 IU dose of human chorionic gonadotropin (hCG) (Serono, Profasi) was administered, and transvaginal follicular aspiration was performed approximately 36 hours after hCG administration. Cumulus from retrieved oocytes were removed by exposing them to 80 Iu/ml hyaluronidase for approximately 30 seconds followed by HEPES-buffered human tubal fluid supplemented with 10% humans serum albumin (HEPES-HTF-HSA) (InVitroCare, Inc., San Diego, Calif., 2002 and 2101).

To accomplish mitotic activation, the cumulus free mature M-II oocytes were treated with 5 µM calcium ionophore (A23187, Sigma) in HEPES-HTF-HSA for 5 minutes at 33° C. followed by 3 washes with HEPES-HTF-HSA and incubation in 1 to 5 mM 6-dimethylaminopurine (6-DMAP, Sigma) in IVC-TWO (InVitroCare, 2008) for 3 to 5 hours at 37° C. The activated oocytes were incubated in IVC-ONE medium (InVitroCare, 2006) for 3 days, and further incubated in IVC-THREE (InVitroCare) for 2 days for cell division and blastocyst-like mass formation.

Alternatively, oocytes were co-cultured with STO mouse feeder cells. On day 6 assisted hatching was performed under a micromanipulator under which a blastocyst-like mass was clamped with the holding pipette (syringe suction system) so that the micro-needle filled with acidified tyrodes solution (Medi-Cult, 1060-0002) at the 3 o'clock position is exposed to the empty perivitelline space to expel the acidified tyrodes solution gently over a small (30 microns) area by holding the needle tip very close to the zona. Expulsion of the acidified tyrodes solution was ceased immediately when the inside of the zona is pierced or softened. The blastocyst-like cell mass would then release from the weakened zona. After blastocyst-like mass detached from zona, immunosurgery was performed to remove trophoblast cells by incubating the mass with anti-human Thy-1 (1:10 dilution in IVC-THREE, Accurate Chemical, Westbury, N.Y. CBL415-CD90) and anti-human lymphocytes (1:10 dilution in IVC-THREE, Accurate Chemical, CL8010) for one hour at 37° C. After washes three times with IVC-THREE medium the blastocyst-like mass was then incubated with LOW-TOX guinea pig complement (1:10 dilution in IVC-THREE, Cedarlane, CL4051) for 30 minutes at 37° C. The complement-treated cell masses were then washed 3 times in the IVC-THREE medium and transferred to a mitomycin-C treated STO (ATCC) feeder cell layer and cultured in stem cell medium consisted of 80% Dulbecco's modified Eagle's medium (no pyruvate, high glucose formulation; Gibco-BRL) supplemented with 20% fetal bovine serum (Gibco-BRL), 1 mM glutamine, 0.1 mM -mercaptoethanol (Sigma), 1% nonessential amino acid stock (Gibco-BRL) and 1,400 U/ml LIF (Chemicon, ESG1106). See FIG. 10A.

Example 1(d)

Development of Blastocyst-Like Cell Masses from Human Post Meiosis I Diploid Oocytes by Activation Followed by Allowing the Extrusion of the Secondary Polar Body and Genomic Self-Replication Procedures for superovulation, oocyte retrieval, and the subsequent removal of cumulus were as described in Example 1(b). To accomplish mitotic activation, the cumulus free mature M-II oocytes were subjected to sham intracytoplasmic sperm injection (ICSI) to mimic activation introduced by sperm followed by incubation with 25 µM calcium iononphore (A23187, Sigma) for 5 minutes at 33° C. Oocytes activated in this manner extrude the secondary polar body and become haploid. Such haploid oocytes were incubated in IVC-ONE medium (InVitroCare, Inc.) for 3 days, and further incubated in IVC-THREE (InVitroCare) for 2 days for cell division and blastocyst-like cell masses formation. The subsequent manipulations of the blastocyst-like mass were as described in Example 1(b). Haploid oocytes resulting from activation are able to self-replicate their genome without cytokinesis and give rise to diploid cells (Taylor, A. S., et al., Hum. Reprod. 9(12):2389–97 (1994); Kaufman, M. H. et al., J. Embryol. Exp. Morphol. 73:249–61 (1983). See FIGS. 10B–D.

Example 1(e)

Mouse HS Cell Growth, Differentiation of such HS Cells under Mouse Kidney Capsule, and Embryoid Body Formation Of Such Cells HS cells obtained from blastocyst-like masses as described in Example 1(a) were seeded on mouse feeder cells in 0.1% gelatin coated dishes (10 cm) with stem cell medium as described in Example 1(a) to colony formation.

One colony of HS cells was dissected into several pieces and implanted in one of the two kidney capsules of 26 hybrid mice to induce stemplasm formation. Stemplasms were then harvested by sacrificing the mice in the post-implantation week 1, 3, 6, 9.5, 10.5, 11, 12, and 14. Half of each stemplasm was fixed in formalin for morphological studies, and the other half was frozen in –80° C. for molecular characterization. Stemplasm started to be formed to a visible size around week three. By staggering the harvesting of stemplasms, various tissue types that developed within the stemplasms were studied. All tissue types identified herein were produced within said stemplasms. Stemplasm genotype was verified by PCR-based allelic analysis described in section C.2., supra.

To create embryoid bodies (EB), HS cells on a 60 mm dish were first washed with PBS twice. 1 ml of Trypsin/EDTA solution was then added, and cells were held at a temperature of 37° C. for five minutes. 5 ml of ES medium was then added, and cells were lifted by a cell scraper and spun down at 1000 rpm for five minutes. The cell pellet thus obtained was then resuspended in 5 ml stem cell medium without LIF, and the cell number was counted. Cells were then seeded onto a suspension dish with lid and vent (Nalge Nunc International, 171099, 35×10 mm) at 2×10⁶/10 cm dish. Cells were fed in stem cell medium for 4 days, where medium was changed every two days by transferring cells into 15 ml tubes, waiting about five minutes until the cells settle to the bottom of the tube, then replacing medium. Cells were then transferred back to the original dish and were allowed to aggregate into embryoid bodies for further differentiation.

Example 1(f)

Differentiation of Human HS Cells within Teratomas, and the Genetic Homozygosity of such Differentiated Tissue.

Thirty-one teratomas were retrieved from the files of the Armed Forces Institute of Pathology, Washington, D.C., and Department of Pathology, New York University. New York, N.Y. (Dr. J. Liu). A variety of different kinds of exclusively differentiated tissue were found in twenty ovarian tumors from female patients. Differentiated tissue was found to be diploid as confirmed by FISH analysis carried out in representative cases using methods known in the art, and alpha-satellite probes to chromosomes 3 and 8. Between 3 and 12 histological areas of undifferentiated and differentiated tissue found in seven ovarian tumors from female patients and four testicular tumors from male patients were identified and selectively microdissected from each case for genetic analysis. In each case, differentiated tissue was found to be genetically homozygous, and undifferentiated tissue was found to be genetically heterozygous.

Microdissection. Unstained 6-micron sections on glass slides were deparaffinized with xylene, rinsed in ethanol from 100% to 80%, briefly stained with hematoxylin and eosin, and rinsed in 10% glycerol in TE buffer. Tissue microdissection was performed under direct light microscopic visualization. From each case, between 6 and 12 areas of different tissue differentiation were separately microdissected for genetic analysis. In addition, several areas of normal, non-neoplastic tissue were procured.

DNA Extraction. Procured cells were immediately resuspended in 25 µl buffer containing Tris-HCl, pH 8.0; 1.0 mM ethylenediamine tetraacetic acid, pH 8.0; 1% Tween 20; and 0.5 mg/ml proteinase K, and were incubated at 37° C. overnight. The mixture was boiled for 5 minutes to inactivate the proteinase K and 1.5 µl of this solution was used for PCR amplification of the DNA.

Genetic Analysis. In order to reliably identify homozygosity in the limited amounts of DNA that were available after microdissection, multiple different microdissected tissue samples were analyzed with up to 14 distinct highly polymorphic microsatellite markers including DIS1646 and D1S243 (1p), D3S2452 (3p), D5S346 (5q), D7S1822 (7q), Ank-1 (8p), D9S171 (9p), D9S303 (9q), Int-2 and PYGM 11q), IFNA (9p), D17S250 (17q), CYP2D (22q), and AR (Xq). Each PCR sample contained 1.5 µl of template DNA as described above, 10 pmol of each primer, 20 nmol each of dATP, dCTP, DGTP, and DTTP, 15 mM $MgCl_2$, 0.1U Taq DNA polymerase, 0.05 ml [$^{32}$P]dCTP (6000 Ci/mmol), and 1 µl of 10× buffer in a total volume of 10 µl. PCR was performed with 35 cycles: denaturing at 95° C. for 1 min, annealing for 1 min (annealing temperature between 55° and 60° C. depending on-the marker) and extending at 72° C. for 60 sec. The final extension was continued for 10 minutes. Labeled amplified DNA was mixed with an equal volume of formamide loading dye (95% formamide, 20 mM EDTA, 0.05% bromophenol blue, and 0.05% xylene cyanol).

Samples can be denatured for 5 min at 95%, loaded onto a gel consisting of 6% acrylamide (acrylamide:bisacrylamide 49:1), and electrophoresed at 1800 V for 90 minutes. After electrophoresis, the gels can be transferred to 3 mm Whatman paper and dried. Autoradiography can be performed with Kodak X-OMAT film (Eastman Kodak, Rochester, N.Y.).

Results. Differentiated teratomous tissue showing consistent homozygosity of the same allele included microdissected samples of squamous epithelium, glia, and cartilage (analyzed with markers Ankl (top) and D1S1646 (bottom)). Normal ovarian tissue was included as control.

In a subset of teratomas, differentiated teratomous tissue found to have discordant homozygous alleles (analyzed with markers Int-2, D9S303, D1S1646, D3S2452, and Ankl) included samples of epidermis, sebaceous gland, respiratory epithelium, and glia. Normal ovarian tissue was included as a control. In such tumors, it is believed that allelic heterozygosity results from the initiation of tumorigenesis before meiosis I in germ cells. After teratogenic tumor cell initiation, random, independent events then lead to progenitor cells with a postmeiotic genotype.

A series of ovarian teratomas and testicular germ cell tumors containing both differentiated and undifferentiated tissue were also analyzed. In each tumor, both undifferentiated and differentiated tissue elements were procured. Homozygous and heterozygous components were detected using markers D3S2452, D3S303, CYP2D, and D17S250. Normal ovarian and testicular tissues were included as controls. Heterozygous alleles were detected in undifferentiated tissue elements including immature squamous epithelium, neural tissue (sometimes from separate areas of neural tissue within the same tumor), cartilage, glandular structures, and mesenchyme. Differentiated tissue elements isolated from the same tumors by microdissection were found to be homozygous for the same markers. Mature elements tested included: sebaceous gland tissue, hair follicle, and mature squamous epithelium (sometimes from separate areas of squamous epithelium within the same tumor). In some tumors, differentiated elements showed opposite homozygous alleles, indicating recombination or suggesting that various elements arose separately from distinct postmeiotic cells.

Example 1(g)

Derivation of Progenitor Cells from Human HS Cells Primary Differentiation

HS cells grown on 60 mm dish (Falcon, #353802) with primary embryonic fibroblast layer and/or 0.1% gelatin coated dishes are trypsinized with 1.5 ml Trypsin/EDTA (Invitrogen, # 25300-050) and transferred to 1.5 ml ES-LIF medium in a 15 ml conical tube. Cells are then spun down at 1200 rpm, and the supernatant is removed. The cell pellet is resuspended into single cell suspension in 2 ml ES-LIF medium, and cultured as suspension cells in suspension culture-35*10 mm-dishes (NalgeNunc, # 171099) at a density of $1–3\times10^6$ cells to allow stem cells to form rounded spherical clusters, known as embryoid bodies (EBs) for 4–6 days. Forming EBs are washed every two days by transferring the EBs to 15 ml conical tubes, and then allowed to settle to the bottom. The supernatant is removed and new ES-LIF is added. EBs are then transferred back into suspension culture dish. HS cells grown as embryoid bodies are comprised of all the germ cell layers, ectodermal, endodermal, and mesodermal.

Ectodermal Progenitors. After 4–6 days, EBs are trypsinized in 1 ml of Trypsin/EDTA, washed in 4 ml ES-LIF medium, and resuspended into single cell suspension in DMEM/Knockout medium (Invitrogen, #10829-018) supplemented with 10% Serum Replacement (Invitrogen, #10828), and G5 (Invitrogen, #17503), N2 (Invitrogen, #I7502-048) or beta NGF (100 ng/ml) (R&D Systems, #256-GF). These cells are cultured at $3–5\times10^5/3$ ml in fibronectin-coated 35 mm dishes (50 ug/ml)(Sigma, #F-0895) for 10 days, with media changes every two-three days.

Alternatively, the EBs are cultured in 0.1% gelatin-coated dish in ES-LIF medium for 1–2 days, and then the medium is changed to serum-free medium supplemented with Insulin (5 ug/ml), Selenium chloride (0.015 nM), Transferrin (50 ug/ml), and fibronectin (5 ug/ml)(Sigma) for 6 days. The cells are trypsinized, and single cell suspensions are cultured in N2 medium (serum free-DMEM/F12 supplemented with N2 (Invitrogen, #I7502-048), B27 (Invitrogen, #I7504-44), and bFGF (10 ng/mL) (Invitrogen, #13256–029)). Cells are then counted and seeded at a density of $2–5\times10^4$ cells/well/ 400 uL N2 medium in 24-well plates pre-coated with poly-L-ornithine (15 ug/ml)(Sigma, #P36550), and expanded for six days.

These progenitors are further differentiated into different neuronal cell types by adding G5, RA, FGF, NGF, GNDF, or BNDF. They are also maintained in their presence conditioned media for cell expansion.

Mesodermal Progenitors. For mesodermal progenitors, the single cell suspension in DMEM/Knockout medium supplemented with 10% Serum Replacement and beta-NGF as described above are cultured for 10 days with media change every two/three days. After this period, the cells are further cultured in Activin A supplemented (20 ng/ml) (Sigma, #A4941) conditioned medium for another 10 days for heart progenitor cells. Alternatively, for kidney and Mullerian duct progenitor cells the cells are further cultured in Activin A supplemented (20 ng/ml) (Sigma, #A4941) conditioned medium for 4–6 days after which 2 ng/ml of TGF-beta (R&D Systems, #) is added to the medium, and the cells are cultured for another 4–6 days.

Endodermal Progenitors. For endodermal progenitors, the single cell suspension in DMEM/Knockout medium supplemented with 10% Serum Replacement, along with G5 or beta-NGF on laminin-coated (10 ug/ml)(Sigma, #L2020), or Collagen I-coated (10 ug/ml)(Sigma, #C-7661) is cultured for 10 days. HGF (20 ng/ml) and/or TGF-alpha (2 ng/ml) are added to the medium to replace G5 or beta-NGF, and the cells are cultured for another 6–8 days.

Alternatively, EBs are plated onto Collagen I-coated dishes and cultured in ES-LIF medium for 4 days. FGF (20 ng/ml) is added and the cells are cultured for another 3 days. After this period, HGF (20 ng/ml) and/or TGF-alpha (2 ng/ml) are added and cultured for another 6 days.

EBs are also transferred to laminin-coated adherent dishes (10 ng/ml) (Sigma, #L2020) or 0.1% gelatin coated 35*10 mm adherent dish, and cultured 1–2 days in ES-LIF medium. The medium is removed and serum-free DMEM/ F12 (Invitrogen, # 11330-0321) medium supplemented with Insulin (5 ug/ml)(Invitrogen, # I1882), Selenium chloride (0.015 nM)(Sigma, #S5261), Transferrin (50 ug/ml) (Sigma, #T-2036), and Fibronectin (5 ug/ml) (Sigma). This medium is designated as ITSFn medium. Cells are fed for 6 days in ITSFn medium, where medium is changed every two days.

Example 1(h)

Development and Isolation of Homozygous Progenitor Cells from Transplanted HS Cells To obtain homozygous progenitor cells, pluripotent HS cells derived from methods disclosed in the foregoing in the foregoing description and examples are transplanted into immuno-compromised mice under kidney capsules and are allowed to grow in vivo for 4 to 6 weeks. The cell mass obtained is then minced into single cells and cultured on feeder cells for further propagation and development into cell lines.

To assess the lineage commitment (the types of progenitor cells), gene expression assays, such as RT-PCR, northern blot, immunohistochemistry, and so forth, are performed for known lineage-specific markers, for example, NF-H, keratin, D-beta-H for the ectoderm, enolase, CMP, rennin, kallikerein, WT1, delta-globin, beta-globin for the mesoderm, and albumin, alpha-1-AT, amylase, PDX-1, insulin, alpha-FP for the endoderm progenitor lineages.

Example 2

Selection of HS Cells Having a Target Immunotype from Populations of HS cells Derived from Material Donated by a Relative (e.g. Parent of the Intended Recipient)

Oocytes are obtained from the recipient's mother by super-ovulation using methods described in the foregoing examples. Once HS cell populations have developed, following methods described in the foregoing examples, a sample of each HS population can be subjected to in vitro differentiation for the optimal expression of HLA molecule (e.g., hemopoietic lineage), the HS-derived sample cells from each population are then tested for HLA-A, -B, and -C specificities using the microlymphotoxicity assay. The test is performed in a 60- or 72 well microlymphotoxicity plate. A panel of antisera, obtained from a commercial source, are selected and prepoured onto the plates and cooled in a −40° or −70° C. freezer. 0.5–1 µl of HS cell suspension (prepared by suspending HS cells in RPMI, or a desired diluent for typing, to $1.5 \times 10^6$ HS-derived sample cells per milliliter using standard techniques) is dispensed into each well of the plate and incubated at 20–22° C. for thirty minutes. 2–5 µl of complement is then added to each well of the plate and incubated at 20–22° C. for sixty minutes. Complement is available commercially as pooled rabbit serum in a freeze-dried form. 1 µl of 5% Eosin solution followed by 1 µl of formaldehyde is then added to each well. Using an appropriate microscope, cell death in each well is established as determined by the amount of dye fixed onto the cells. A standard scoring system is used, from 0 to 8, where 8 is 80–100% representing a strong positive, and 2 is 20–40% representing a doubtful positive.

The sample cells are then tested for HLA-DR, -DQ and -DB using PCR-RFLP analysis. DNA is extracted from HS cells using standard procedures known in the art. Extracted DNA, 200–300 ng, is then amplified by PCR with 2.5 U of the Taq polymerase. PCR primers used for amplification of HLA class II are listed in FIG. 11. After amplification, 4–7 µl of a reaction mixture are added to a solution containing a restriction enzyme chosen from the list in FIG. 5, and an appropriate restriction buffer, and incubated for 3 hrs. Twenty-nine different enzymes are used for full class II typing. Samples of the amplified DNAs cleaved by restriction enzymes are then subjected to electrophoresis using a 12% polyacrylamide horizontal gel in a mini-apparatus (e.g. Mupid-2 obtained from E-Y laboratories Inc., San Mateo, Calif.). RFLP fragments are detected by staining with ethidium bromide.

The immunotype of the recipient is determined using the serological and molecular methodology described above. 20 ml of venous blood is obtained from the recipient (target) into sodium citrate anticoagulant (1 ml of 3.3% sodium citrate per 10 ml of blood.) The citrated blood is then diluted with an equal volume of heparinized HBSS (1 ml of 1000 U/ml heparin to 100 ml of HBSS). A 10 ml volume of diluted blood is layered onto 4 ml of Ficoll-isopaque in 17–120 mm screw top centrifuge tubes using a pipette. The tubes are then centrifuged at 700×g for fifteen to twenty minutes. Red blood cell and polymorphonuclear cells form a pellet at the end of the tube, and lymphocytes form a discrete layer at the interface of Ficoll-isopaque. The lymphocyte layer is aspirated into another tube, topped off with HBSS, and centrifuged again at 250×g for five minutes. The lymphocyte pellet is then resuspended, washed with HBSS, and centrifuged again at 120×g for five minutes. This step separates most of the platelets, suspended in the supernatant, while pelleting the lymphocytes at the bottom of the tube. The HBSS is discarded, and the lymphocyte pellet is resuspended in HBSS, and spun for the last time at 250×g for five minutes. The HBSS is then discarded, and the lymphocyte pellet is resuspended in RPMI or a desired diluent for typing. HLA-A, B and C typing procedure described above with the sample stem is repeated to determine the target HLA-haplotype.

Another 20 ml or less of venous blood is obtained from the recipient for molecular typing of HLA class II. Genomic DNA extracted from the blood cell of the recipient using techniques known in the art is amplified using PCR. An RFLP analysis as described above is then performed.

The recipient's HLA haplotype may be homozygous or heterozygous, and in either situation one HLA haplotype (e.g., maternal II) will match with one of the HS cell populations derived from the mother's oocytes. Once a HS population is determined to have the target immunotype, it may then be differentiated in vivo, or in vitro using the techniques described in U.S. patent application Ser. No. 09/997,240, and U.S. Provisional Application Ser. No. 60/253,943, fully incorporated by reference herein, and transplanted into the recipient.

Example 3

Selection of HS Cells Having Target Genotype from Populations of HS Cells Derived from Material Extracted from Intended Recipient (Self Donor)

In those instances where the intended recipient of the transplant suffers from a genetic disorder linked to the expression of a mutant gene sequence, it becomes necessary to select the population of HS cells that are homozygous for non-mutant haplotype (e.g., the "target" genotype). An exemplary protocol for the selection for genotype is as follows:

In this example, the intended recipient is a women afflicted with sickle cell anemia, A number of human disease states have been attributed to genetic mutations effecting one or more of the genes encoding hemoglobin polypeptide chains, including sickle cell anemia, which results from a point mutation in the hemoglobin β-chain. The genetic sequence of the mutant gene associated with sickle cell anemia has been disclosed and extensively studied. See, for example, Saiki et al., 1985, *Science,* 230, 1350–1354, incorporated by reference herein.

A series of populations of HS cells are created from oocytes harvested from the intended recipient according to the procedures described above in Example 1. The populations are then assayed for genotype. Only those populations that homogeneously carry the target genotype (e.g., the normal or wild type gene rather than the mutant gene) are selected for further development.

In this example, the mutant gene associated with sickle cell anemia is detected by allele-specific hybridization, or "ASH." This technology is based on the stable annealing of a short, single-stranded oligonucleotide probe to a single-stranded target nucleic acid only when base pairing is completely complementary. The hybridization can then be detected from a radioactive or non-radioactive label on the probe (methods of labeling probes and other nucleic acids are set forth in detail below). ASH markers are used as dominant markers where the presence or absence of only one allele (or haplotype) is determined from hybridization or lack of hybridization by only one probe. The alternative allele may be inferred from the lack of hybridization.

ASH markers have been developed to diagnose susceptibility to human diseases caused by point mutations in DNA sequence. An ASH marker useful in detecting the $\beta^s$-globin allele associated with sickle-cell anemia is described by Conner et al., Proc. Natl. Acad. Sci. USA 80:278–282, 1983 and incorporated by reference herein.

Cell samples are taken from each HS population and genomic DNA is extracted using conventional methodology. Following the procedures outlined by Conner et al., supra, the genomic DNA is digested with restriction endonucleases. The resulting nucleic acid fragments are amplified using PCR (see Mullis, K. B. et al., Methods Enzymol. 155:335–350 (1987) incorporated by reference herein) to create amplicons. The amplicons are then transferred to a membrane having a radio-labeled oligonucleotide probe specific for sickle cell anemia bound thereto in a dot-blot format. Hybridization dots are detected by autoradiography. Alternatively, the amplicons can be labeled, and the probes membrane bound.

Once a sample is determined to have the target immunotype and genotype, it may then be differentiated in vivo or in vitro, using the techniques described in U.S. patent application Ser. No. 09/997,240, and U.S. Provisional Application Ser. No. 60/253,943 incorporated by reference herein, and transplanted into the intended recipient.

For male recipients and female recipient who are not suitable for self-donors due to medical conditions, HS cells having both the target immunotype and genotypes can be derived from female family member donors. Once a sample population is determined to have the target immunotype and genotype, it may then be differentiated in vivo or in vitro, using the techniques described in U.S. patent application Ser. No. 09/997,240, and U.S. Provisional Application Ser. No. 60/253,943 incorporated by reference herein, and transplanted into the intended recipient.

Example 4

Selection of HS Cells Having a Target Immunotype and a Target Genotype from Populations of HS Cells Derived from Material Donated by A Non-Related Individual (Non-Self, Non-Relative Donor)

In certain instances, donor material cannot be obtained from the intended recipient or a close relative. In such cases, it may be necessary to screen the HS populations both for target immunotype and for target genotype. An exemplary protocol for the selection for target immunotype and target genotype is as follows.

Populations of HS cells are derived from oocytes extracted from the donor individual using the protocol cited above in Example 1. Once HS cell populations have developed, sample cells are typed for HLA-A, -B, and -C specificities using the microlyphotoxicity assay described in Example 2 above.

HS cells are further typed to HLA class II antigens using the PCR-SSOP procedure. DNA is extracted from the cells using standard procedures known in the art. Extracted DNA, 200–300 ng, is then amplified by PCR with 2.5 U of the Taq polymerase. PCR primers used for amplification of HLA-DRB/DQB/DPB, and cycling conditions for all primer combinations for oligotyping are listed in FIG. 14. 2.5 µl aliquots of the reaction mixture are then mixed with 50 µl NH$_4$-acetate 1M, and manually applied on a filter (Nytran, Schleicher & Schuell) using a Minifold II stot blotter (Schleicher & Schuell). The membranes are denatured by placing them in 0.4 N NaOH, for ten minutes, then neutralized for 10 minutes in 1M NH$_4$-acetate, and then dried at room temperature. Positive and negative controls for hybridization are included on each membrane.

Oligonucleotides for hybridization are then labeled with [$^{32}$P]γ-ATP and polynucleotide kinase, in a 10 µl reaction. The reaction contains 6 pmol oligo, 25 µCi ATP, 1 µl kinase buffer (0.5 M tris-HCL, pH 7.6, 0.1 M MgCl$_2$, 50 mM dithiothreitol (DTT), 1 mM spermidine, 1 mM EDTA), and 5UT4 polynucleotide kinase (Pharmacia). The reaction is incubated for thirty minutes at 37° C., and the labeled oligo is purified on a DE52 column (Whatman, Cat. No. 4057-050). After loading the column, the oligo is washed with 10 ml washing buffer (150 mM NaCl, 20 mM Tris-HCl, pH 7.8, 10 mM EDTA), and then eluted with 0.2-ml fractions of elution buffer (1M NaCl, 20 mM Tris-HCL, pH 7.8, 1 mM EDTA).

Each membrane is then hybridized with radioactive oligos. First, a prehybridization step is performed for thirty minutes at 54° C. with tetramethylammonium chloride hybridization (TMAC) buffer (50 mM Tris-HCl, pH 8.0, 3M TMAC (Fluka), 2 mM EDTA, pH 8.0, 5× Denhardt's, 0.1% Na-dodecyl sulphate, 100 µg/ml denatured salmon sperm DNA, filtered through Whatman 3 MM paper). The membranes are then hybridized for one to three hours in a TMAC hybridization buffer containing 0.5×10$^6$ cpm/ml of the labeled oligo at 54° C. The blots are washed twice for ten minutes at room temperature in a TMAC washing buffer, and then twice again for fifteen minutes at 59° C. (19-mers) in the same. The procedure is fully described in Hui et al., Handbook, at 119–123, incorporated by reference herein.

The target immunotype is determined using the serological and molecular methodology described above in Example 2 above. Target haplotype may be homozygous or heterozygous. In either situation there is a high probability that at least one HLA haplotype of the recipient will match the HLA of a sample HS population derived from the populations of cells from unrelated oocyte donors of the same ethnicity as the recipient (See above).

In this invention, unrelated women afflicted with genetic diseases do not need to be excluded since HS cells with the absence of disease genotype can be derived. For example, the foreign donor (e.g., the unrelated individual) is a women afflicted with beta-thalassemia. Beta-thalassemia is a genetically determined defect in hemoglobin synthesis. There is an inability to manufacture sufficient quantities of globin chains. Alpha-and beta-thalassemia conditions are blood-related disorders which result from genetic mutations manifested phenotypically by deficient synthesis of one type of globin chain, resulting in excess synthesis of the other type of globin chain. See generally Weatherall et al., The Thalassaemia Syndromes, 3rd ed., Oxford, Blackwell Scientific, 1981 and U.S. Pat. No. 5,750,345. The $\beta^0$-thalassemia allele associated with β-thalassemia is described by Pirastu et al., New England J. Med. 309:284–287, 1983 incorporated by reference herein. Thus, in the context of this example, the "target" genotype will be the absence of the $\beta^0$-thalassemia allele, the mutant haplotype associated with pathology.

In assaying for genotype, only those populations that homogeneously carry the target genotype (e.g., the normal or wild type gene rather than the mutant gene) are selected for further development. The target genotype, e.g., the absence of the gene corresponding to beta-thalassemia, is detected and selected by a procedure analogous to that described in Example 3 above with respect to sickle cell anemia, using an ASH probe specific for beta-thalassemia (see Weatherall et al. and Piratsu et al., supra.).

Once a sample population is determined to have the target immunotype and genotype, it may then be differentiated in vivo or in vitro, using the techniques described in U.S. patent application Ser. No. 09/997,240, and U.S. Provisional Application Ser. No. 60/253,943 incorporated by reference herein, and transplanted into the intended recipient.

The invention claimed is:

1. A method for producing a mammalian homozygous embryonic stem (HES) cell depository, wherein each HES cell produces a cell line, which has alleles that are homozygous for a Major Histocompatibility Complex (MHC) haplotype, wherein the method comprises:
   (a) selecting donors;
   (b) determining the MHC haplotype of each donor;
   (c) mitotically activating non-fertilized post-meiosis I diploid oocytes obtained from each donor to develop multiple blastocyst-like masses, each of which contains an inner cell mass (ICM) that is homozygous for a particular MHC haplotype, wherein the non-fertilized post-meiosis I diploid oocytes are subject to sham intracytoplasmic sperm injection (ICSI) followed by incubation with calcium ionophore;
   (d) isolating HES cells from the ICM obtained from each donor;
   (e) culturing the isolated HES cells to obtain HES cell lines;
   (f) determining the MHC haplotype of each HES cell line; and
   (g) cataloging the MHC haplotype of each HES cell line obtained in (e).

2. The method of claim 1, wherein the donors are human.

3. The method of claim 1, wherein the donors are non-human.

* * * * *